United States Patent [19]
Tanaka et al.

[11] Patent Number: 5,283,349
[45] Date of Patent: Feb. 1, 1994

[54] 2,6,7-TRISUBSTITUTED-3-METHYLENEBICYCLO(3.3.0)-OCTANES, AND PROCESS FOR PRODUCTION THEREOF

[75] Inventors: Toshio Tanaka; Kiyoshi Bannai, both of Hino; Seizi Kurozumi, Kokubunji, all of Japan

[73] Assignee: Teijin Limited, Osaka, Japan

[21] Appl. No.: 905,976

[22] Filed: Sep. 11, 1986

[30] Foreign Application Priority Data

Sep. 13, 1985 [JP] Japan .................. 60-201716
Oct. 14, 1985 [JP] Japan .................. 60-226973
Oct. 14, 1985 [JP] Japan .................. 60-226974

[51] Int. Cl.$^5$ .................. C07F 7/08; C07F 7/18
[52] U.S. Cl. .................. 556/436; 556/443; 556/445; 556/446; 568/15; 568/28; 568/31; 568/33; 568/374; 568/591; 568/665; 560/256; 549/214; 549/421; 549/475
[58] Field of Search .............. 556/436, 443, 445, 446; 549/214, 475, 421; 560/256; 568/15, 28, 31, 33, 374, 591, 665

[56] References Cited

U.S. PATENT DOCUMENTS

| 4,346,041 | 8/1982 | Aristoff ............... | 556/436 X |
| 4,359,581 | 11/1982 | Skuballa et al. ....... | 556/436 X |
| 4,505,905 | 3/1985 | Boswell et al. ........ | 556/436 X |
| 4,554,363 | 11/1985 | Vorbrueggen .......... | 556/436 X |
| 4,644,068 | 2/1987 | Shibasaki et al. ...... | 556/436 X |
| 4,681,951 | 7/1987 | Shibasaki et al. ...... | 556/436 X |

FOREIGN PATENT DOCUMENTS

0247740 4/1987 European Pat. Off. .

OTHER PUBLICATIONS

The Journal of the Chemical Society, Chemical Communications, No. 23, Aug. 1984, pp. 1602–1603.
Chemical Abstracts, vol. 103, No. 25, Feb. 1985, p. 871.

*Primary Examiner*—Paul F. Shaver
*Attorney, Agent, or Firm*—Sherman and Shalloway

[57] ABSTRACT

A 2,6,7-trisubstituted-3-methylenebicyclo-[3.3.0]octane of formula (I) or an enantiomer thereof, or a mixture of these in an arbitrary ratio. The compound is a key intermediate for preparation of isocarbacyclins which are useful as medicines for the circulatory system such as an antithrombotic agent, an antilipidemic agent, a hypotensive agent or an antiarterosclerotic agent.

21 Claims, No Drawings

2,6,7-TRISUBSTITUTED-3-METHYLENEBICYCLO(3.3.0)-OCTANES, AND PROCESS FOR PRODUCTION THEREOF

This invention relates to 2,6,7-trisubstituted-3-methylenebicyclo[3.3.0]octanes and a process for production thereof. More specifically, this invention relates to 2,6,7-trisubstituted-3-methylenebicylco[3.3.0]octanes, novel key intermediates for synthesis of isocarbacyclins, i.e. 9(0)-methano-Δ$^{6(9\alpha)}$-prostaglandins I$_1$.

Carbacyclins are prostaglandin I$_2$ analogs resulting from substitution of methylene groups for the oxygen atoms at the 6,9-positions of prostaglandin (to be sometimes abbreviated as PG) I$_2$ (PGI$_2$), an in vivo physiologically active substance. Since carbacyclins are chemically more stable than natural prostaglandin I$_2$ having an enol ether partial structure in the molecule, they are useful as pharmaceuticals such as an antithrombotic agent. It was recently discovered that isocarbacyclins, a double bond isomer of carbacyclin, namely 9(0)-methano-Δ$^{6(9\alpha)}$-prostaglandins I$_1$, show the strongest platelet aggregation inhibitory activity among these analogs, and are expected to have application as medicines [see Ikegami et al., Tetrahedron Letters, 33, 3493 and 3497 (1983)].

Several examples of the production of the 9(0)-methano-Δ$^{6(9\alpha)}$-prostaglandin I$_1$ (isocarbacyclin) have previously been known. The outlines of the methods, key synthetic intermediates used in these examples and the literature references describing them are summarized as follows:

(1) Ikegami et al. Testrahedron Letters, 24, 3493 (1983) and Chemistry Letters, 1069 (1984):

PGE$_2$ $\xrightarrow{\text{several steps}}$

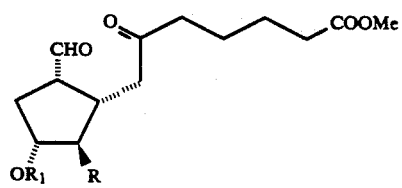

$\xrightarrow{\text{3 steps}}$

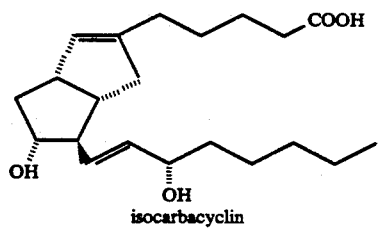
isocarbacyclin (2) Ikegami et al. Tetrahedron Letters, 24, 3497 (1983)

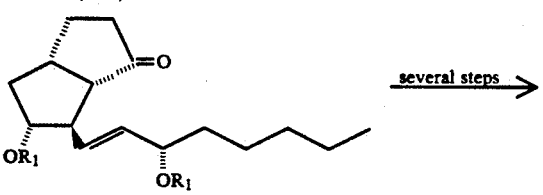
$\xrightarrow{\text{several steps}}$
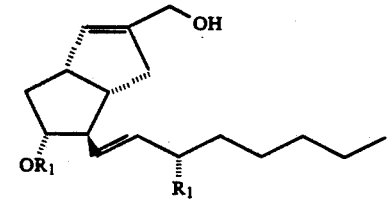
$\xrightarrow{\text{several steps}}$

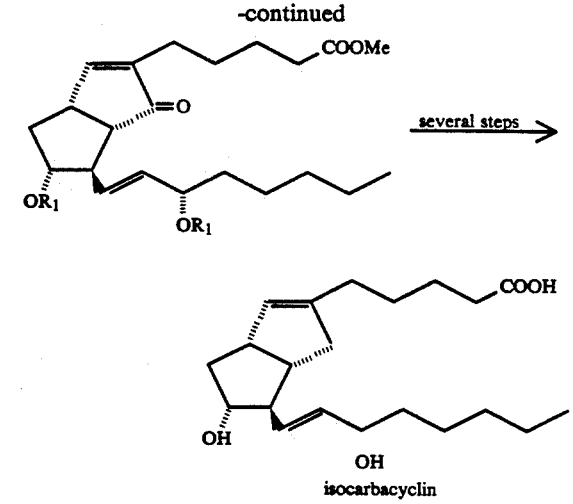
isocarbacyclin (3) Ikegami et al., J. Chem. Soc., Chemical Communications, 1602 (1984):

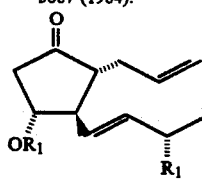
$\xrightarrow{\text{several steps}}$
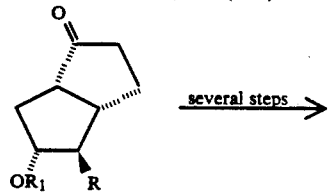
$\xrightarrow{\text{several steps}}$
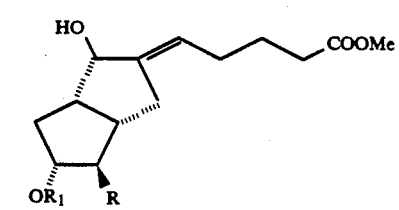
isocarbacyclin (4) Shibasaki et al., Tetrahedron Letters, 25, 5087 (1984):

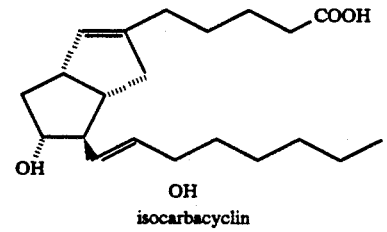
$\xrightarrow{\text{several steps}}$
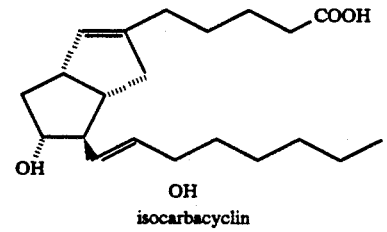
$\xrightarrow{\text{several steps}}$ -continued

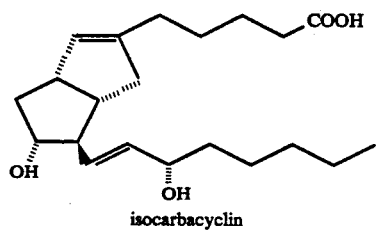
isocarbacyclin (5) Shibasaki et al., Tetrahedron Letters, 25, 1067 (1984):

PGE$_2$ —several steps→

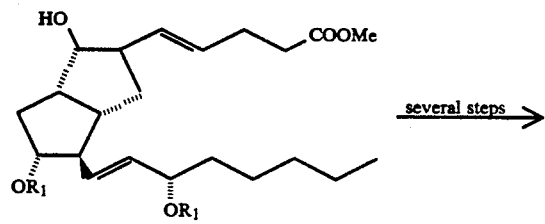

several steps→ isocarbacyclin (6) Kojima et al., Chem. Pharm. Bull., 32, 2866 (1984):

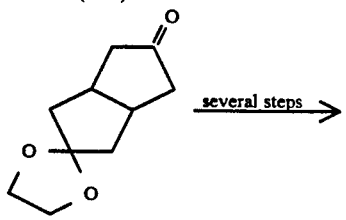

several steps→

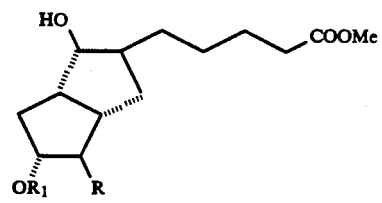

several steps→

+ enantiomer thereof (±)-isocarbacyclin (7) Kojima et al., Japanese Laid-Open Patent Publication No. 28943/1985:

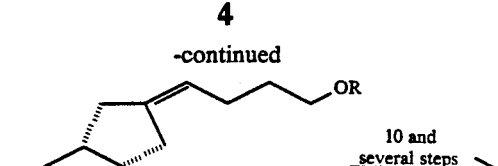

10 and several steps→

(±)

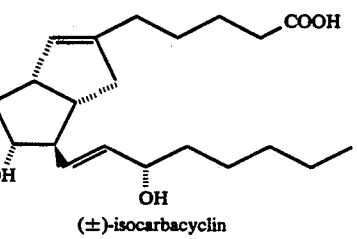

+ enantiomorph thereof (±)-isocarbacyclin

Methods (1) and (5) uses PGE$_2$ as a starting material, and through several steps, it is converted to a key intermediate, and after further several steps, the final product, isocarbacyclin, is obtained.

Methods (2) and (3) require a multiplicity of steps starting from expensive Corey lactone in order to obtain the corresponding starting materials and key intermediates, and the total yield of the final product is not high.

According to methods (6) and (7), the final product is obtained only in the form of a DL isomer.

Finally, method (4) has the great disadvantage that the total yield is decreased since in the steps from the key intermediate to the final isocarbacyclin, various difficulties arise such as the use of an organic mercury compound, the loss of the regiospecificity of the compounds, and the inclusion of inseparable by-products.

It is an object of this invention to provide novel key intermediates for the synthesis of 9(0)-methano-Δ$^{6(9\alpha)}$-prostaglandins I$_1$ (isocarbacyclins), and a process for production thereof.

Another object of this invention is to provide 2,6,7-trisubstituted-3-methylenebicyclo[3.3.0]octanes and 3,6,7-trisubstituted-2,3-epoxybicyclo[3.3.0]octanes as the aforesaid key intermediates, and a process for production thereof.

Still another object of this invention is to provide a process for producing isocarbacyclins from the key intermediates highly regioelectively in high yields with industrial advantages.

Further objects and advantages of this invention will become apparent from the following description.

According to this invention, these objects and advantages are achieved by a 2,6,7-trisubstituted-3-methylenebicyclo[3.3.0]octane which is a compound represented by the following formula (I)

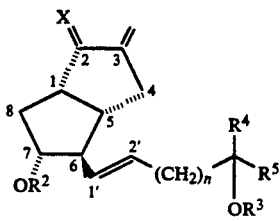

(I)

wherein R$^2$ and R$^3$ are identical or different and each represents a hydrogen atom, a tri(C$_1$-C$_7$)hydrocarbonsilyl group or a group forming an acetal linkage together with the oxygen atom of the hydroxyl group; $R^4$ represents a hydrogen atom, a methyl group or a vinyl group; $R^5$ represents an unsubstituted linear or branched $C_3$–$C_8$ alkyl group which may be interrupted by an oxygen atom, a substituted linear or branched $C_1$–$C_5$ alkyl group in which the substituent is a $C_1$–$C_6$ alkoxy group or a phenyl, phenoxy or $C_3$–$C_{10}$ cycloalkyl group which may be substituted further, a phenyl group which may be substituted, a phenoxy group which may be substituted, or a $C_3$–$C_{10}$ cycloalkyl group which may be substituted; n is 0 or 1; and X= represents an oxo group (O=) or a group of the formula

in which $R^1$ represents a hydrogen atom, a tri-($C_1$–$C_7$-)hydrocarbonsilyl group, a group forming an acetal linkage together with the oxygen atom of the hydroxyl group, a $C_2$–$C_{10}$ acyl group, a ($C_1$–$C_{10}$)hydrocarbonsulfonyl group, or a di-($C_1$–$C_{10}$)hydrocarbonphosphoryl group, an enantiomer thereof, or a mixture of these in arbitrary ratios.

In formula (I), $R^2$ and $R^3$ are identical or different, and each represents a hydrogen atom, a tri($C_1$–$C_7$) hydrocarbonsilyl group or a group forming an acetal linkage together with the oxygen atom of the hydroxyl group.

Preferred examples of the tri($C_1$–$C_7$) hydrocarbonsilyl group include tri($C_1$–$C_4$)alkylsilyl groups such as trimethylsilyl, triethylsilyl, triisopropylsilyl and t-butyldimethylsilyl groups; diphenyl($C_1$–$C_4$)alkylsilyl groups such as a t-butyldiphenylsilyl group, di($C_1$–$C_4$)alkylphenylsilyl groups such as a dimethylphenylsilyl group; and a tribenzylsilyl group. The tri($C_1$–$C_4$)alkylsilyl, diphenyl($C_1$–$C_4$)alkylsilyl and phenyldi($C_1$–$C_4$)alkylsilyl groups are preferred. Among them, t-butyldimethylsilyl and trimethylsilyl groups are especially preferred.

Examples of the group forming an acetal linkage together with the oxygen atom of the hydroxyl group include methoxymethyl, 1-ethoxyethyl, 2-methoxy-2-propyl, 2-ethoxy-2-propyl, (2-methoxyethoxy)methyl, benzyloxymethyl, 2-tetrahydropyranyl, 2-tetrahydrofuranyl and 6,6-dimethyl-3-oxa-2-oxobicyclo[3.1.0-]hex-4-yl groups. The 2-tetrahydropyranyl, 2-tetrahydrofuranyl, 1-ethoxyethyl, 2-ethoxy-2-propyl, (2-methoxyethoxy)methyl, and 6,6-dimethyl-3-oxa-2-oxobicyclo[3.1.0]hex-4-yl groups are preferred. The 2-tetrahydropyranyl group is especially preferred.

It should be understood that these silyl groups and the groups forming an acetal linkage are protective groups for the hydroxyl group. These protective groups can be easily removed under weakly acidic to neutral conditions in the stage of the final product to provide free hydroxyl groups useful in drugs. Hence, protective groups for the hydroxyl group which have such properties may be used instead of the silyl group or the acetal linkage-forming group.

In formula (I), $R^4$ represents a hydrogen atom, a methyl group or a vinyl group.

In formula (I), $R^5$ represents an unsubstituted linear or branched $C_3$–$C_8$ alkyl group which may be interrupted by an oxygen atom, a substituted linear or branched $C_1$–$C_5$ alkyl group; a phenyl group which may be substituted, a phenoxy group which may be substituted, or a $C_3$–$C_{10}$ cycloalkyl group which may be substituted.

Examples of the unsubstituted linear or branched $C_3$–$C_8$ alkyl group which may be interrupted by an oxygen atom include 2-methoxyethyl, 2-ethoxyethyl, propyl, butyl, pentyl, hexyl, heptyl, 2-hexyl, 2-methyl-2-hexyl, 2-methylbutyl, 2-methylpentyl, 2-methylhexyl and 2,2-dimethylhexyl groups. Of these, butyl, pentyl, hexyl, heptyl, 2-hexyl, 2-methyl-2-hexyl, 2-methylbutyl and 2-methylpentyl groups are preferred.

Examples of the substituted linear or branched substituted $C_1$–$C_5$ alkyl groups include methyl, ethyl, propyl, propyl, isopropyl, butyl, isobutyl, sec-butyl, t-butyl and pentyl groups which are substituted by a phenyl, phenoxy or $C_3$–$C_8$ cycloalkyl group which may further be substituted.

In the optionally substituted phenyl, phenoxy or $C_3$–$C_8$ cycloalkyl group and in the identically named groups for $R^5$, the substituent in the substituted phenyl, substituted phenoxy or substituted $C_3$–$C_{10}$ cycloalkyl groups may include, for example, halogen atoms, protected hydroxyl groups (such as tri($C_1$–$C_7$)hydrocarbonsilyloxy groups and $C_3$–$C_8$ alkoxy groups), and $C_1$–$C_4$ alkyl groups. Examples of the $C_3$–$C_{10}$ cycloalkyl groups include cyclopropyl, cyclopentyl, cyclohexyl, cyclohexenyl, cycloheptyl, cyclooctyl and cyclodecyl groups. The cyclopentyl and cyclohexyl groups are preferred. Examples of the $C_1$–$C_6$ alkoxy groups are methoxy, ethoxy, propyloxy, isopropyloxy, butoxy, t-butoxy and hexyloxy groups.

The tri($C_1$–$C_7$)hydrocarbonsilyloxy groups may, for example, be silyloxy groups corresponding to the tri($C_2$–$C_7$)hydrocarbonsilyl groups exemplified hereinabove for $R^2$ and $R^3$.

Examples of the $C_1$–$C_4$ alkyl group are methyl, ethyl, n-propyl, iso-propyl, n-butyl, sec-butyl and t-butyl groups.

Examples of the linear or branched substituted $C_1$–$C_5$ alkyl group include butyl, pentyl, hexyl, heptyl, 2-hexyl, 2-methyl-2-hexyl, 2-methylbutyl, 2-methylpentyl, cyclopentyl, cyclohexyl, phenyl, phenoxy, cyclopentylmethyl, and cyclohexylmethyl groups. The substituent may be attached to an arbitrary position of the alkyl group.

In formula (I), n represents 0 or 1.

Furthermore, in formula (I), X= represents an oxo group (O=) or the group

$R^1$ represents a hydrogen atom, a tri($C_1$–$C_7$)hydrocarbonsilyl group, a group forming an acetal linkage together with the oxygen atom of the hydroxyl group, a $C_2$–$C_{10}$ acyl group, a ($C_1$–$C_{10}$)hydrocarbonsulfonyl group, or a di($C_1$–$C_6$)hydrocarbonphosphoryl group.

Examples of the tri($C_1$–$C_7$)hydrocarbonsilyl group and the acetal linkage-forming group may be the same as those given hereinabove with regard to $R^2$ and $R^3$. Examples of the $C_2$–$C_{10}$ acyl group are acetyl, propionyl, butyryl, isobutyryl, valeryl, isovaleryl, pivaloyl, hexanoyl, heptanoyl, cyclopentylcarbonyl, cyclohexanecarbonyl, benzoyl and 2,4,6-trimethylbenzoyl group. Of these, the acetyl, propyl and pivaloyl groups are preferred. Examples of the ($C_1$–$C_{10}$)hydrocarbonsulfonyl group include methanesulfonyl, ethanesulfonyl, isopropylsulfonyl, butanesulfonyl, benzenesulfonyl, p-toluenesulfonyl, d-10-camphorsulfonyl, 1-naphthalenesulfonyl, and 2-naphthalenesulfonyl groups. Of these, the methanesulfonyl and p-toluenesulfonyl groups are preferred.

Examples of the di($C_1$-$C_6$)hydrocarbonphosphoryl group are diethylphosphoryl and diphenylphosphoryl groups.

When X= is

in formula (I), the group $R^1O$ may be alpha- (i.e. $R^1O$...) or beta- (i.e.

)

to the cyclopentane ring to which it is bonded, or a mixture of alpha- and beta- in an arbitrary ratio.

The 2,6,7-trisubstituted-3-methylenebicyclo[3.3.0]octane provided by this invention may be the compound represented by formula (I) above, or its enantiomorph, or a mixture of these isomers in an arbitrary ratio.

Preferred examples of the 2,6,7-trisubstituted-3-methylenebicyclo[3.3.0]octanes of formula (I) provided by this invention are given below.

(I) Specific examples of compounds of formula (I) in which n is 0

(101) (1S,5S,6S,7R)-2-oxo-3-methylene-6-[(E,3S)-3-hydroxy-1-octenyl]-7-hydroxybicyclo[3.3.0]octane, (102) (1S,5S,6S,7R)-2-oxo-3-methylene-6-[(E,3S)-3-hydroxy-5-ethoxy-1-pentenyl]-7-hydroxybicyclo[3.3.0]octane, (103) (1S,5S,6S,7R)-2-oxo-3-methylene-6-[(E,3S)-3-hydroxy-5-phenoxy-1-pentenyl]-7-hydroxybicyclo[3.3.0]octane, (104) (1S,5S,6S,7R)-2-oxo-3-methylene-6-[(E,3S)-3-hydroxy-4-(m-chlorophenoxy-1-butenyl]-7-hydroxybicyclo-3.3.0]octane, (105) (1S,5S,6S,7R)-2-oxo-3-methylene-5-[(E,3S)-3-hydroxy-1-nonenyl]-7-hydroxybicyclo[3.3.0]octane, (106) (1S,5S,6S,7R)-2-oxo-3-methylene-6-[(E,3S)-3-hydroxy-1-decenyl]-7-hydroxybicyclo[3.3.0]octane, (107) (1S,5S,6S,7R)-2-oxo-3-methylene-6-[(E,3S)-3-hydroxy-5-methyl-1-nonenyl]-7-hydroxybicyclo[3.3.0]octane, (108) (1S,5S,6S,7R)-2-oxo-3-methylene-6-[(E,3S,5R)-3-hydroxy-5-methyl-1-nonenyl]-7-hydroxybicyclo[3.3.0]octane, (109) (1S,5S,6S,7R)-2-oxo-3-methylene-6-[(E,3S,5S)-3-hydroxy-5-methyl-1-nonenyl]-7-hydroxybicyclo[3.3.0]octane, (110) (1S,5S,6S,7R)-2-oxo-3-methylene-6-[(E,3S)-3-hydroxy-5,5-dimethyl-1-octenyl]-7-hydroxybicyclo[3.3.0]octane, (111) (1S,5S,6S,7R)-2-oxo-3-methylene-6-[(E,3S)-3-hydroxy-3-cyclopentyl-1-propenyl]-7-hydroxybicyclo]3.3.0]octane, (112) (1S,5S,6S,7R)-2-oxo-3-methylene-6-[(E,3S)-3-hydroxy-3-cyclohexyl-1-propenyl]-7-hydroxybicyclo[3.3.0]octane, (113) (1S,5S,6S,7R)-2-oxo-3-methylene-6-[(E,3S)-3-hydroxy-4-cyclopentyl-1-butenyl]-7-hydroxybicyclo[3.3.0]octane, (114) (1S,5S,6S,7R)-2-oxo-3-methylene-6-[(E,3S)-3-hydroxy-4-cyclohexyl-1-buenyl]-7-hydroxybicyclo[3.3.0]octane, (115) (1S,5S,6S,7R)-2-oxo-3-methylene-6-[(E)-3-hydroxy-3-methyl-1-octenyl]-7-hydroxybicyclo[3.3.0]octane, (116) (1S,5S,6S,7R)-2-oxo-3-methylene-6-[(E)-3-hydroxy-3-methyl-5-ethoxy-1-pentenyl]-7-hydroxybicyclo[3.3.0]octane, (117) (1S,5S,6S,7R)-2-oxo-3-methylene-6-[(E)-3-hydroxy-3-methyl-1-nonyl]-7-hydroxybicyclo[3.3.0]octane, (118) (1S,5S,6S,7R)-2-oxo-3-methylene-6-[(E)-3-hydroxy-3,5-dimethyl-1-nonenyl]-7-hydroxybicyclo[3.3.0]octane, (119) (1S,5S,6S,7R)-2-oxo-3-methylene-6-[(E,3S)-3-hydroxy-4-methyl-1-octenyl]-7-hydroxybicyclo[3.3.0]octane, (120) (1S,5S,6S,7R)-2-oxo-3-methylene-6-[(E,3S)-3-hydroxy-4,4-dimethyl-1-octenyl]-7-hydroxybicyclo[3.3.0]octane, (121) (1S,5S,6S,7R)-2-oxo-3-methylene-6-[(E)-3-hydroxy-3-vinyl-1-octenyl]-7-hydroxybicyclo[3.3.0]octane, (122) (1S,5S,6S,7R)-2-oxo-3-methylene-6-[(E)-3-vinyl-1-nonenyl]-7-hydroxybicyclo[3.3.0]octane, (123) (1S,5S,6S,7R)-2-oxo-3-methylene-6-[(E)-3-methyl-1-nonenyl]-7-hydroxybicyclo[3.3.0]octane, (124) (1S,5S,6S,7R)-2-oxo-3-methylene-6-[(1E,3S)-3-hydroxy-7-methyl-1,6-octadienyl]-7-hydroxybicyclo[3.3.0]octane, (125) (1S,5S,6S,7R)-2-oxo-3-methylene-6-[(1E,3S)-3-hydroxy-8-methyl-1,7-nonadienyl]-7-hydroxybicyclo[3.3.0]octane, (126) (1S,5S,6S,7R)-2-oxo-3-methylene-6-[(1E,3S)-3-hydroxy-9-methyl-1,8-decanedienyl]-7-hydroxybicyclo[3.3.0]octane, (127) Compounds (101) to (126) having a (2R)-hydroxyl group resulting from reduction of the 2-oxo group, (128) Compounds (101) to (126) having a (2S)-hydroxyl group resulting from reduction of the 2-oxo group, (129) Compounds (101) to (126) having a (2RS)-hydroxyl group resulting from reduction of the 2-oxo group, (130) 3',7-bis(t-butyldimethylsilyl)ethers of compounds (101) to (126), (131) 3',7-bis(2-tetrahydropyranyl)ethers of compounds (101) to (126), (132) 3'-t-butyldimethylsilyl-7-(2-tetrahydropyranyl)ethers of compounds (101) to (126), (133) 3'-(2-tetrahydropyrany)-7-t-butyldimethylsilyl ethers of compounds (101) to (126), (134) ethers resulting from protection of the hydroxyl groups at the 3',7-positions in compounds (127) to (129) with a t-butyldimethylsilyl group and/or a 2-tetrahydropyranyl group, (135) ethers resulting from protection of the hydroxyl group at the 2-position in compounds (127) to (129) and (134) by a trimethylsilyl group, (136) ethers resulting from protection of the hydroxyl group at the 2-position in compounds (127) to (129) and (134) with a t-butyldimethylsilyl group, (137) the ethers resulting from protection of the hydroxyl group at the 2-position in compounds (127) to (129) and (134) with a 2-tetrahydropyranyl group, (138) esters resulting from protection of the hydroxyl group at the 2-position in compounds (127) to (129) and (134) with an acetyl group,
(139) esters resulting from protection of the hydroxyl group at the 2-position in compounds (127) to (129) and (134) with a propionyl group,
(140) esters resulting from protection of the hydroxyl group at the 2-position in compounds (127) to (129) and (134) with a pivaloyl group,
(141) esters resulting from protection of the hydroxyl group at the 2-position in compounds (127) to (129) and (134) with a 2,4,6-trimethylbenzoyl group,
(142) esters resulting from protection of the hydroxyl group at the 2-position in compounds (127) to (129) and (134) with a methanesulfonyl group,
(143) esters resulting from protection of the hydroxyl group at the 2-position in compounds (127) to (129) and (134) with a p-toluenesulfonyl group, and
(144) esters resulting from protection of the hydroxyl group at the 2-position in compounds (127) to (129) and (134) with a diphenylphosphoryl group.

(II) Specific examples of compounds of formula (I) in which n is 1
(201) (1S,5S,6S,7R)-2-oxo-3-methylene-6-[(E)-4-hydroxy-1-octenyl]-7-hydroxybicyclo[3.3.0]octane,
(202) (1S,5S,6S,7R)-2-oxo-3-methylene-6-[(E)-4-hydroxy-5-ethoxy-1-pentenyl]-7-hydroxybicyclo[3.3.0]octane, (203) (1S,5S,6S,7R)-2-oxo-3-methylene-6-[(E)-4-hydroxy-5-phenoxy-1-pentenyl]-7-hydroxybicyclo-[3.3.0]octane,
(204) (1S,5S,6S,7R)-2-oxo-3-methylene-6-[(E)-4-hydroxy-1-nonenyl]-7-hydroxybicyclo[3.3.0]octane,
(205) (1S,5S,6S,7R)-2-oxo-3-methylene-6-[(E)-4-hydroxy-1-decenyl]-7-hydroxybicyclo]3.3.0]octane,
(206) (1S,5S,6S,7R)-2-oxo-3-methylene-6-[(E)-4-hydroxy-5-methyl-1-nonenyl]-7-hydroxybicyclo[3.3.0]octane,
(207) (1S,5S,6S,7R)-2-oxo-3-methylene-6-[(E)-4-hydroxy-5,5-dimethyl-1-octenyl]-7-hydroxybicyclo[3.3.0]octane,
(208) (1S,5S,6S,7R)-2-oxo-3-methylene-6-[(E)-4-hydroxy-4-cyclopentyl-1-butenyl]-7-hydroxybicyclo[3.3.0]octane,
(209) (1S,5S,6S,7R)-2-oxo-3-methylene-6-[(E)-4-hydroxy-4-cyclohexyl-1-butenyl]-7-hydroxybicyclo[3.3.0]octane,
(210) (1S,5S,6S,7R)-2-oxo-3-methylene-6-[(E)-4-hydroxy-4-methyl-1-octenyl]-7-hydroxybicyclo[3.3.0]octane,
(211) (1S,5S,6S,7R)-2-oxo-3-methylene-6-[(E,4S)-4-hydroxy-4-methyl-1-octenyl]-7-hydroxybicyclo[3.3.0]octane,
(212) (1S,5S,6S,7R)-2-oxo-3-methylene-6-[(E,4R)-4-hydroxy-4-methyl-1-octenyl]-7-hydroxybicyclo[3.3.0]octane,
(213) (1S,5S,6S,7R)-2-oxo-3-methylene-6-[(E)-4-hydroxy-4-methyl-5-ethoxy-1-pentenyl]-7-hydroxybicyclo[3.3.0]octane,
(214) (1S,5S,6S,7R)-2-oxo-3-methylene-6-[(E)-4-hydroxy-4-methyl-5-phenoxy-1-methyl-5-phenoxy-1-pentenyl]-7-hydroxybicyclo]3.3.0]octane,
(215) (1S,5S,6S,7S)-2-oxo-3-methylene-6-[(E)-4-hydroxy-4-methyl-1-nonenyl]-7-hydroxybicyclo[3.3.0]octane,
(216) (1S,5S,6S,7R)-2-oxo-3-methylene-6-[(E)-4-hydroxy-4,5-dimethyl-1-nonenyl]-7-hydroxybicyclo[3.3.0]octane,
(217) (1S,5S,6S,7R)-6-[(E)-4-hydroxy-5-methyl-1-octenyl]-7-hydroxybicyclo[3.3.0]octane,
(218) (1S,5S,6S,7R)-2-oxo-3-methylene-6-[(E)-4-hydroxy-4-methyl-4-cyclopentyl-1-butenyl]-7-hydroxybicyclo[3.3.0]octane,
(219) (1S,5S,6S,7R)-2-oxo-3-methylene-6-[(E)-4-hydroxy-4-methyl-4-cyclohexyl-1-butenyl]-7-hydroxybicyclo[3.3.0]octane,
(220) (1S,5S,6S,7R)-2-oxo-3-methylene-6-[(E)-4-hydroxy-4-vinyl-1-octenyl]-7-hydroxybicyclo[3.3.0]octane,
(221) (1S,5S,6S,7S)-2-oxo-3-methylene-6-[(E)-4-hydroxy-4-vinyl-5-ethoxy-1-pentenyl]-7-hydroxybicyclo[3.3.0]octane,
(222) (1S,5S,6S,7R)-2-oxo-3-methylene-6-[(E)-4-hydroxy-4-vinyl-5-phenoxy-1-pentenyl1-7-hydroxybicyclo[3.3.0]octane,
(223) (1S,5S,6S,7R)-2-oxo-3-methylene-6-[(E)-4-hydroxy-4-vinyl-1-nonenyl]-7-hydroxybicyclo[3.3.0]octane,
(224) (1S,5S,6S,7R)-2-oxo-3-methylene-6-[(E)-4-hydroxy-4-vinyl-5-methyl-1-nonenyl]-7-hydroxybicyclo[13. 3. 01 octane,
(225) (1S,5S,6S,7R)-2-oxo-3-methylene-6-[(E)-4-hydroxy-4-vinyl-4-cyclopentyl-1-butenyl]-7-hydroxybicyclo[3.3.0]octane,
(226) (1S,5S,6S,7R)-2-oxo-3-methylene-6-[(E)-4-hydroxy-4-vinyl-4-cyclohexyl-1-butenyl]-7-hydroxybicyclo[3.3.0]octane,
(227) (1S,5S,6S,7R)-2-oxo-3-methylene-6-[(E)-4-hydroxy-7-methyl-1,6-octadienyl]-7-hydroxybicyclo[3.3.0]octane,
(228) (1S,5S,6S,7R)-2-oxo-3-methylene-6-[(E)-4-hydroxy-6-methyl-1,7-nonadienyl]-7-hydroxybicyclo[3.3. 01 octane,
(229) (1S,5S,6S,7R)-2-oxo-3-methylene-6-[(E)-4-3-hydroxy-9-methyl-1,8-decanedienyl]-7-hydroxybicyclo[3.3.0]octane,
(230) Compounds (201) to (229) having a (2R)-hydroxyl group resulting from reduction of the 2-oxo group,
(231) Compounds (201) to (229) having a (2S)-hydroxyl group resulting from reduction of the 2-oxo group,
(232) Compounds (201) to (229) having a (2RS)-hydroxyl group resulting from reduction of the 2-oxo group,
(233) 4',7-bis(t-butyldimethylsilyl)ethers of compounds (201) to (220),
(234) 4',7-bis(2-tetrahydropyranyl)ethers of compounds (201) to (229),
(235) 4'-t-butyldimethylsilyl-7-(2-tetrahydropyranyl)ethers of compounds (201) to (229),
(236) 4'-(2-tetrahydropyranyl)-7-t-butyldimethylsilyl ethers of compounds (201) to (229),
(237) ethers resulting from protection of the hydroxyl groups at the 4',7-positions of compounds (230) to (232) with a t-butyldimethylsilyl group and/or a 2-tetrahydropyranyl group,
(238) ethers resulting from protection of the hydroxyl group at the 2-position in compounds (230) to (232) and (237) with a trimethylsilyl group,
(239) ethers resulting from protection of the hydroxyl group at the 2-position in compounds (230) to (232) and (237) with a t-butyldimethylsilyl group,
(240) ethers resulting from protection of the hydroxyl group at the 2-position in compounds (230) to (232) and (237) with a 2-tetrahydropyranyl group, (241) esters resulting from protection of the hydroxyl group at the 2-position in compounds (230) to (232) and (237) with an acetyl group,
(242) esters resulting from protection of the hydroxyl group at the 2-position in compounds (230) to (232) and (237) with a propionyl group,
(243) esters resulting from protection of the hydroxyl group at the 2-position in compounds (230) to (232) and (237) with a pivaloyl group.
(244) esters resulting from protection of the hydroxyl group at the 2-position in compounds (230) to (232) and (237) with a 2,4,6-trimethylbenzoyl group,
(245) esters resulting from protection of the hydroxyl group at the 2-position in compounds (230) to (232) and (237) with a methanesulfonyl group,
(246) esters resulting from protection of the hydroxyl group at the 2-position in compounds (230) to (232) and (237) with a p-toluenesulfonyl group, and
(247) esters resulting from protection of the hydroxyl group at the 2-position in compounds (230)-(232) and (237) with a diphenylphosphonyl group.

According to this invention, the 2,6,7-trisubstituted-3-methylenebicyclo[3.3.0]octane can be produced as follows:

group), a phenyl group which may be substituted, a phenoxy group which may be substituted, or a $C_3$-$C_{10}$ cycloalkyl group which may be substituted.

Specific preferred examples of these groups may be the same as those given hereinabove with regard to $R^5$ in formula (I).

In formula (V), n is 0 or 1.

In step 1, the 3,6,7-trisubstituted-bicyclo[3.3.0]-2-octene is 2,3-epoxidized. Suitable epoxidizing agents that may be used in this step include, for example, hydrogen peroxide, organic peroxides such as t-butyl hydroperoxide and cumene hydroperoxide, and organic acids such as m-chloroperbenzoic acid, perbenzoic acid, monoperoxyphthalic acid and peracetic acid (oxidizing agents), which are used in the presence of catalysts such as selenium dioxide, tungstic acid, tungstate salts, molybdate salts, vanadium oxide, iron (III)/acetylacetone complex or titanium salts.

In view of the fact that the chemical structure of that part of the compound represented by (V) which is to be oxidized is allyl alcohol, t-butyl hydroperoxide, for example, is especially preferably used in the presence of a catalyst such as tungstic acid, a tungstate salt, a molybdate salt (such as molybdenum hexacarbonyl), a vana- Reaction Scheme 1

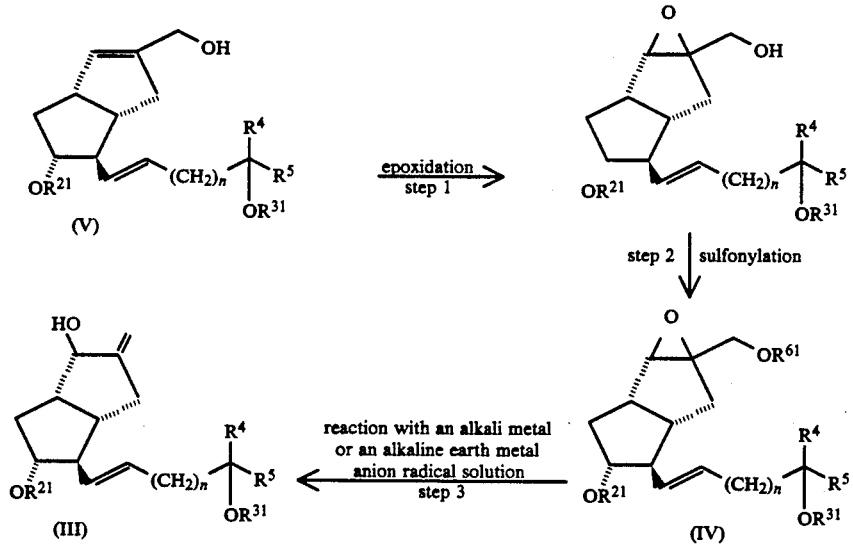

The individual steps in Reaction Scheme 1 will be described below.

Step 1 (epoxidation)

The 3,6,7-trisubstituted-bicyclo[3.3.0]-2-octene used as a starting material in step 1 is represented by formula (V). This compound is known.

In formula (V), $R^{21}$ and R 31 are identical or different, and each represents a tri($C_1$-$C_7$)hydrocarbonsilyl group or a group forming an acetal linkage with the oxygen atom of the hydroxyl groupp. Preferred examples of these groups may be the same as those given hereinabove with regard to $R^2$ and $R^3$ in formula (I). $R^4$ in formula (V) represents a hydrogen atom, a methyl group or a vinyl group. $R^5$ represents an unsubstituted linear or branched unsubstituted $C_3$-$C_8$ alkyl group which may be interrupted by an oxygen atom, a substituted linear or branched $C_1$-$C_6$ alkyl group (wherein the substituent is a $C_1$-$C_6$ alkoxy group or an optionally substituted phenyl, phenoxy or $C_3$-$C_{10}$ cycloalkyl dium oxide (V) salt (such as vanadyl acetylacetonate) or a titanium salt (such as titanium tetraisopropoxide).

In step 1, the 3,6,7-trisubstituted-bicyclo[3.3.0]-2-octene is reacted with the epoxidizing agent (an oxidizing agent and optionally an oxidation catalyst therefor) and an inert organic medium.

Stoichiometrically, the 3,6,7-trisubstituted-bicyclo[3.3.0]-2-octene and the oxidizing agent react in equimolar proportions. Usually, the reaction is carried out by using 0.5 to 5.0 moles, preferably 0.8 to 3.0 moles, especially preferably 1.0 to 2.0 moles, per mole of the 3,6,7-trisubstituted-bicyclo[3.3.0]-2-octene, of the oxidizing agent.

Where the oxidation catalyst is used, its amount varies slightly depending upon its kind. Usually, it is used in an amount of 0.001 to 1.2 moles.

The reaction temperature, which varies depending upon the kind of the epoxidizing agent (the oxidizing agent and optionally the oxidation catalyst therefor), is usually −100° to 1000° C., preferably −78° to 800° C., especially preferably about −20° to 500° C. The reaction time likewise varies depending upon the epoxidizing agent and the reaction temperature. It is usually sufficient that the reaction is carried out for several hours at −20° to 500° C.

The reaction is carried out in the presence of an inert organic medium. Examples of the inert organic medium are saturated hydrocarbons such as pentane, hexane, heptane and cyclohexane, aromatic hydrocarbons such as benzene, toluene and xylene, ethers such as diethyl ether, tetrahydrofuran, dioxane, dimethoxyethane and diethylene glycol dimethyl ether, and halogenated hydrocarbons such as methylene chloride and chloroform.

The amount of the inert organic medium is one sufficient to cause the reaction to proceed smoothly. Usually, it is used in an amount 1 to 100 times, preferably 2 to 20 times, the volume of the starting material.

The resulting reaction mixture is worked up by ordinary methods. For example, a sparingly water-soluble organic solvent such as hexane, pentane, petroleum ether, diethyl ether or ethyl acetate is added to the reaction mixture. Alternatively, the reaction mixture is directly concentrated under reduced pressure, and then the organic solvent is added. The organic mixture obtained is then washed with an aqueous sodium chloride solution as required, and dried over a desiccant such as anhydrous magnesium sulfate, anhydrous sodium sulfate or anhydrous calcium chloride. The organic medium is then concentrated under reduced pressure to form a crude product. As required, the crude product may be purified by purifying means such as column chromatography, thin-layer chromatography, or liquid chromatography.

As a result, a 3,6,7-trisubstituted-2,3-epoxybicyclo[3.3.0]-2-octane of formula (IV') in which $R^6$ is a hydrogen atom is obtained.

Step 2 (sulfonylation)

The 2,3-epoxy octane of formula (IV') in which $R^6$ is a hydrogen atom is then sulfonylated in step 2.

Sulfonylation is a known reaction, and may be carried out by reacting the 2,3-epoxide with a ($C_1$–$C_{10}$) hydrocarbon sulfonyl chloride in the presence of a basic substance in an organic medium.

Examples of the basic substance used in the above reaction are pyridine, 4-(N,N-dimethylamino)pyridine, triethylamine, tributylamine and trimethylenediamine. The basic substance is used in an amount of 1.0 to 3.0 moles, preferably 1.2 to 1.5 moles, per mole of the 2,3-epoxide. The organic medium may be the same as the inert organic medium used in step 1. Its amount is one sufficient to cause the reaction to proceed smoothly. Usually, the amount of the organic medium is 1 to 100 times, preferably 2 to 20 times, the volume of the starting compound.

Examples of the ($C_1$–$C_{10}$)hydrocarbonsulfonyl chloride include methanesulfonyl chloride, benzenesulfonyl chloride, p-toluenesulfonyl chloride, naphthalenesulfonyl chloride and camphor-sulfonyl chloride. The amount of the sulfonyl chloride is 1.0 to 2.0 moles, preferably 1.1 to 1.5 moles, per mole of the 2,3-epoxide.

The reaction temperature is −100° to 1000° C., preferably −78° to 80° C., especially preferably −50° to 300° C. The reaction time which varies depending upon the reaction temperature is usually several hours at a temperature of −40° to 25° C.

After the reaction, the reaction mixture may be worked up, and the product isolated, as in step 1. As a result, a 3,6,7-trisubstituted-2,3-epoxybicyclo[3.3.0]octane of formula (IV) can be obtained.

The 2,3-epoxide used as the starting material in step 2 and the 2,3-epoxide of formula (IV) obtained in step 2 are novel compounds provided for the first time by the present inventors.

Compounds represented by the following formula (IV')

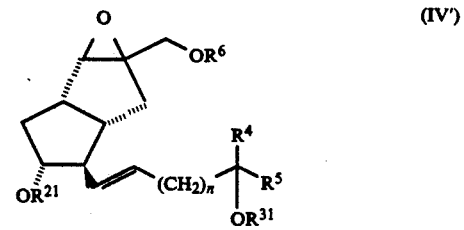

wherein $R^{21}$ and $R^{31}$ are identical or different and each represents a tri($C_1$–$C_7$)hydrocarbonsilyl or a group forming an acetal linkage together with the oxygen atom of the hydroxyl group, $R^4$, $R^5$ and n are the same as defined above, and $R^6$ represents a hydrogen atom or a ($C_1$–$C_{10}$)hydrocarbonsulfonyl group, which embrace the aforesaid 2,3-epoxides, or antiomers thereof, or mixtures of these in arbitrary ratios constitute part of the 3,6,7-trisubstituted-2,3-epoxybicyclo[3.3.0]octanes provided by this invention.

Step 3 (reaction with a solution of an alkali metal or alkaline earth metal anion radical)

Step 3 is performed by reacting the 3,6,7-trisubstituted-2,3-epoxybicyclo[3.3.0]octane of formula (IV) obtained in step 2 with a solution of an alkali metal or alkaline earth metal anion radical solution.

The alkali metal in the anion radical solution may include lithium, sodium and potassium. Sodium is especially preferred. Calcium is especially preferred as the alkaline earth metal. The amount of the alkali metal or alkaline earth metal used is 1.0 to 20.0 moles, preferably 1.2 to 10.0 moles, per mole of the 3,6,7-trisubstituted-2,3-epoxybicyclo[3.3.0]octane of formula (IV).

A preferred solvent for the anion radical solution is, for example, an ether solvent such as diethyl ether, tetrahydrofuran or dimethoxyethane containing liquid ammonia, naphthalene, 1-(N,N-dimethylamino)naphthalene or 4,4'-di-t-butylbiphenyl in an amount of at least 1 mole per mole of the alkali metal or the alkaline earth metal. Tetrahydrofuran containing liquid ammonia or naphthalene is most preferred. The amount of the solvent may be one sufficient to cause the reaction to proceed smoothly. Usually, its amount is 1 to 100 times, preferably 2 to 20 times, the volume of the starting compound.

The reaction temperature is −100° to 1000° C., preferably −78° to 500° C., especially preferably −20° to 300° C. The reaction time, which varies depending upon the reaction temperature, is usually within several hours at 0° to 300° C.

After the reaction, the reaction mixture is worked up, and the product isolated, as in step 1. As a result, a 6,7-disubstituted-2-hydroxy-3-methylenebicyclo[3.3.0]octane of formula (III) is obtained.

The 3,6,7-trisubstituted-bicyclo[3.3.0]-2-octene of formula (V) used as the starting material in step 1 can be produced, for example, by the same method as that described in Shibasaki et al., Tetrahedron Letters, 25, 5087 (1984). This production process is briefly shown by the following Reaction Scheme 2.

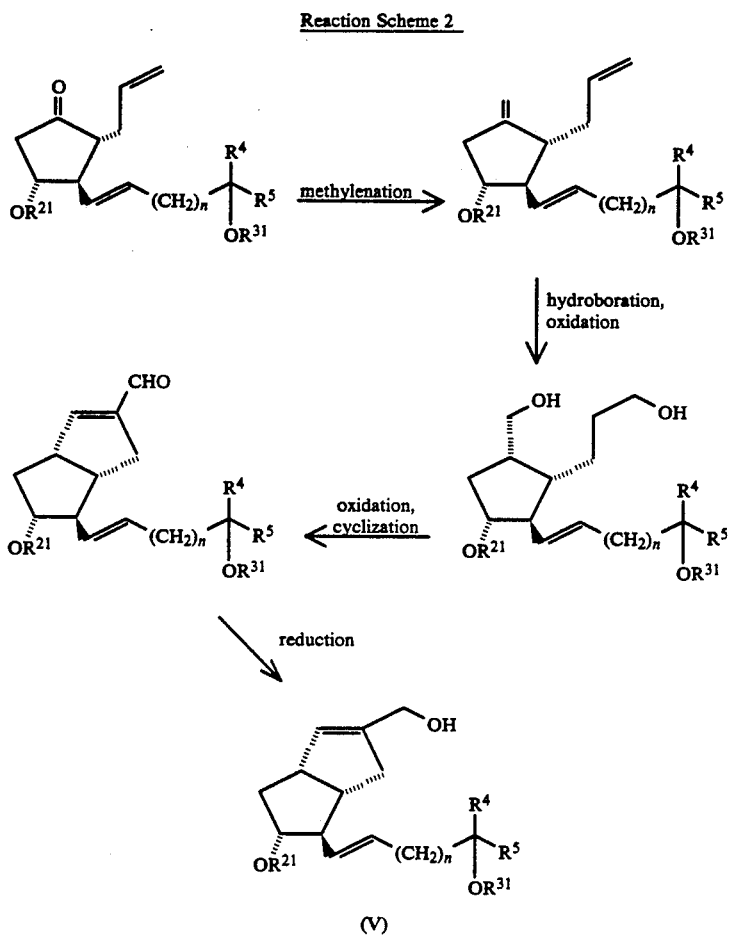

Reaction Scheme 2

In accordance with Reaction Scheme 3 shown below. The compound of formula (III) constituting part of the 2,6,7-trisubstituted-3-methylenebicyclo[3.3.0]octane provided by this invention gives useful isocarbacyclins, enantiomers thereof, or mixtures of these in arbitrary ratios.

Reaction Scheme 3

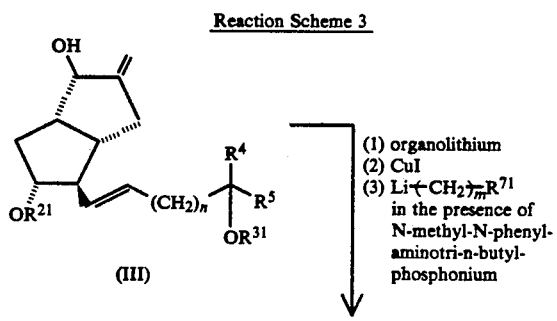

(1) organolithium
(2) CuI
(3) Li$(CH_2)_m R^{71}$
in the presence of N-methyl-N-phenyl-aminotri-n-butyl-phosphonium

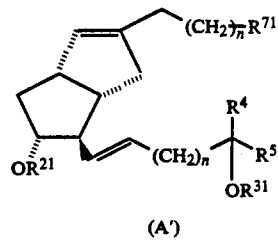

(A')

Reaction Scheme 3 will be described below.

In formula (III), $R^{21}$ and $R^{31}$ are identical or different and each represents a tri($C_1$-$C_7$)hydrocarbon silyl group or a group forming an acetal linkage together with the oxygen atom of the hydroxyl group. Examples of these groups are the same as those given hereinabove for $R^2$ and $R^3$ in formula (I).

In formula (III), $R^4$ represents a hydrogen atom, a methyl group or a vinyl group. $R^5$ represents an unsubstituted linear or branched $C_3$-$C_8$ alkyl group which may be interrupted by an oxygen atom, a substituted linear or branched $C_1$-$C_5$ alkyl group (wherein the substituent is a $C_1$-$C_6$ alkoxy group or an optionally substituted phenyl, phenoxy or $C_3$-$C_{10}$ cycloalkyl group), a phenyl group which may be substituted, a phenoxy group which may be substituted, or a $C_3$-$C_{10}$ cycloalkyl group. Preferred examples of these groups are the same as those given hereinabove to $R^5$ in formula (I).

In formula (III), n is 0 or 1.

In the above reaction, the 6,7-disubstituted-2-hydroxy-3-methylenebicyclo[3.3.0]octane of formula (III) is reacted with an organolithium in an organic medium, then with cuprous iodide and further with an organolithium compound of formula (II) in the presence of N-methyl-N-phenylaminotributylphosphonium iodide.

The above reaction is carried out in accordance with the method of Y. Tanigawa et al. described in J. Am. Chem. Soc., 100, 4610 (1978).

n-Butyllithium and methyllithium, for example, may be used preferably as the organolithium used in the reaction. The amount of the organolithium is 0.8 to 1.5 times, preferably 1.0 to 1.2 moles, per mole of the 6,7-disubstituted-2-hydroxy-3-methylenebicyclo[3.3.0]octane. The reaction temperature is $-78°$ C. to 50° C., preferably $-40°$ to 25° C. The reaction time, which varies depending upon the reaction temperature, is, for example, about 30 minutes at 200° C. By this reaction, the 6,7-disubstituted-2-hydroxy-3-methylenebicyclo[3.3.0]octane of formula (III) changes to its lithium alkoxide.

Thereafter, the resulting lithium alkoxide solution is reacted with cuprous iodide with a solution of an organic copper lithium compound. The amount of cuprous iodide is 0.8 to 1.5 moles, preferably 1.0 to 1.2 moles, per mole of the compound of formula (III). The reaction temperature is $-100°$ to 50° C., preferably $-78°$ to 25° C. The reaction time, which varies depending upon the reaction temperature, is about s at 20° C.

An organic lithium compound of the following formula (II)

$$Li\text{+}CH_2\text{)}_{\overline{m}}R^{71} \qquad (II)$$

wherein $R^{71}$ represents a hydrogen atom, a $C_2$–$C_6$ saturated hydrocarbon group or functionalized groups convertible into carboxyl group and m is an integer of 1 to 6, is further added to the resulting organic copper lithium compound solution, and the reaction is carried out.

In formula (II), examples of the $C_2$–$C_6$ saturated hydrocarbon group are ethyl, cyclopentyl and cyclohexyl groups. As for the functionalized groups convertible into carboxyl group, the $C_2$–$C_6$ unsaturated hydocarbon groups such as vinyl, ethynyl and phenyl groups are mentioned first. The vinyl groups is most preferred in order to convert the reaction product into a 9(0)-methano-$\Delta^{6(9\alpha)}$-prostaglandin $I_1$ (isocarbacyclin) [M. Shibasaki et al., Tetrahedron Letters, 25, 5087 (1984)]. At this time, m is is preferably 2. As for the functionalized groups convertible into carboxyl group, a protected hydroxyl group is mentioned. The protected hydroxyl group may be the same protected hydroxyl groups as exemplified hereinabove for $R^{21}$ and $R^{31}$. These protected hydroxyl groups are also preferred because they can be easily converted into the hydroxyl group and further converted into the 9(0)-methano-$\Delta^{6(9\alpha)}$-prostaglandin $I_1$ (isocarbacyclin). At this time, m is preferably 4.

The functionalized groups well known in the reports such as Tetrahedron Letters 24, 5571 (1983) [E. J. Corey et al.], Synthesis, 153 (1974) [R. H. De Wolfe] and J. Chem. Soc. Chem. Comm., 207 (1980) [B. T. Golding et al.] can be also used as the functionalized groups convertible into carboxylic groups in the instant invention. At this time, m is preferably 3.

These organic lithium compounds can be easily obtained from the corresponding bromides and iodides by reaction with t-butyllithium or a lithium anion radical solution (such as naphthalene, I-(N,N-dimethylamino)-naphthalene, 4,4'-di-t-butylbiphenyl, or ammonia).

The amount of the organic lithium compound used is 0.8 to 20.0 moles, preferably 1.0 to 10.0 moles, especially preferably 1.2 to 5.0 moles, per mole of the compound of formula (1). The reaction temperature is $-100°$ to 0° C., preferably $-78°$ to $-40°$ C. The reaction time is about 10 to 30 minutes.

The reaction is finally carried out by adding N-methyl-N-phenylaminotributylphosphonium iodide. A method of synthesizing this reagent is reported in the above-cited reference of Y. Tanigawa et al. Preferably, this reagent is added in the form of a solution in N,N-dimethylformamide.

The amount of this reagent used is 0.8 to 5.0 moles, preferably 1.0 to 3.0 moles, especially preferably 1.1 to 2.0 moles, per mole of the compound of formula (I). The reaction temperature is $-100°$ to 50° C., preferably $-78°$ to 25° C. The reaction time is several hours at 25° C.

The reaction using this reagent is carried out in an organic medium from the initial stage. Examples of the organic medium include hexane, benzene, ether, tetrahydrofuran, dimethoxyethane, dioxane, methylene chloride, and N,N-dimethylformamide. They may be used singly or in combination. Hexane, tetrahydrofuran and N,N-dimethylformamide are especially preferred. The amount of the organic medium is 1.0 to 100.0 times, preferably 5.0 to 50.0 times, the volume of the reaction substance.

The reaction mixture so obtained is worked up in a usual manner. For example, a sparingly water-soluble organic solvent such as hexane, pentane, petroleum ether, ethyl ether or ethyl acetate is added. The separated organic mixture is washed with an aqueous sodium chloride solution as required, and dried over a desiccant such as anhydrous magnesium sulfate, anhydrous sodium sulfate or anhydrous calcium chloride. The organic medium is then removed under reduced pressure to give a crude product. The crude product, if required, may be purified by purifying means such as column chromatography, thin-layer chromatography, or liquid chromatography.

Thus, in accordance with the reactions in Reaction Scheme 3, the compound of formula (A') given above is obtained.

If required, by subjecting the compound of formula (A') to deprotection, hydrolysis, esterification and/or salt forming reaction, the groups $R^{21}$, $R^{31}$ and $R^{71}$ can be converted to form an isocarbacyclin represented by the following formula (A)

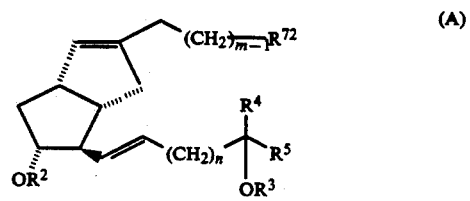

wherein $R^{72}$ represents $-CH_2-R^{71}$, hydroxymethyl group, 3-hydroxypropyl group, carboxyl group, carboxymethyl group, 2-carboxyethyl group, and salts or esters of these carboxyl groups; $R^{71}$, $R^2$, $R^3$, $R^4$, $R^5$, m and n are as defined above.

The deprotection reaction, i.e. the removal of the protective group for the hydroxyl group may be conveniently carried out by using a catalyst such as acetic acid, pyridinium p-toluenesulfonate or a cation exchange resin in a reaction medium such as water, tetrahydrofuran, ethyl ether, dioxane, acetone or acetonitrile if the protective group is a group forming an acetal linkage together with the oxygen atom of the hydroxyl group. The reaction is usually carried out at $-78°$ to $+30°$ C. for about 10 minutes to 3 days. If the protective group is a tri($C_1$-$C_7$)hydrocarbonsilyl group the deprotection reaction can be carried out at the same temperature for the same period of time in the aforesaid reaction solvent in the presence of, for example, acetic acid, tetrabutylammonium fluoride, cerium fluoride, aqueous hydrogen fluoride or pyridine-hydrogen fluoride.

When the functionalized groups except those mentioned above are used, these functionalized groups can be converted into corresponding carboxy-containing groups according to the procedures disclosed in the literature cited hereinbefore for exemplifying the functionalized groups.

The compound having the carboxyl group formed as a result of hydrolysis as mentioned above is then subjected, as required, to esterification or a salt-forming reaction to give the corresponding ester or carboxylate salt.

The esterification is a known reaction, and can be carried out by reacting the compound with an excessive amount of an alcohol in the presence of an acid catalyst such as p-toluenesulfonic acid, a pyridium salt thereof, sulfuric acid, or a cation exchange resin and a dehydrocondensing agent such as N,N'-dicyclohexylcarbodiimide or isobutyl chloroformate. Methyl-esterification may also be carried out by reacting the compound with an excessive amount of methyl iodide (preferably in the presence of acetonitile as a solvent) in the presence of an organic base such as diisopropylethylamine or diazomethane.

The salt-forming reaction is also known per se, and may be carried out by reacting the compound with a nearly equal amount of a basic compound such as potassium hydroxide, sodium hydroxide or sodium carbonate or ammonia, trimethylamine, monoethanolamine or morpholine by an ordinary method.

Thus, the isocarbocyclins of formula (A), its enantiomers or an isomeric mixture thereof in an arbitrary ratio can be produced in accordance with Reaction Scheme 3 from the corresponding starting material.

The process for producing the isocarbacyclins in accordance with Reaction Scheme 3 has the great industrial advantage that the starting material can be easily obtained industrially, synthesis of the skeleton of the compounds can be carried out sterospecifically and regiospecifically, the yield of the final product is high, and these final product can be easily isolated.

Reaction Schemes 4 and 5 starting from the compound of formula (III) also give useful novel compounds as is the compound (III).

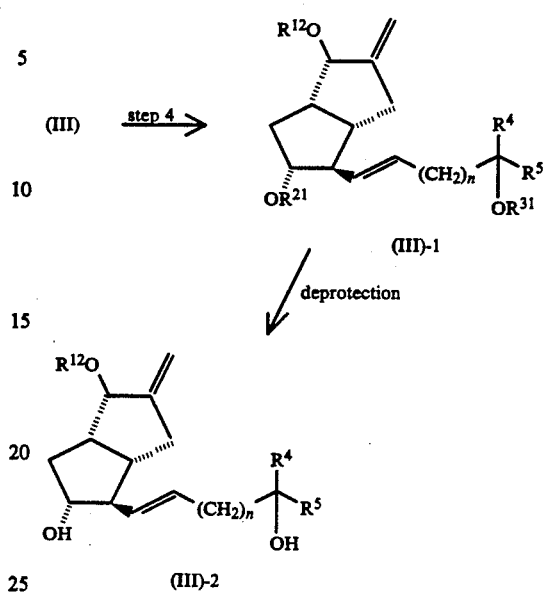

Reaction Scheme 4

Step 4 (reaction with the hydroxyl group)

The hydrogen atom of the hydroxyl group at the 2-position of the 6,7-disubstituted-2-hydroxy-3-methylenebicyclo[3.3.0]octane of formula (III) obtained in step 3 may be substituted by a substituent ($R^{12}$) by methods known per se. The substituent $R^{12}$ may be formed by tri($C_1$-$C_7$)hydrocarbonsilyl etherification [for example, reaction with a tri($C_1$-$C_7$)hydrocarbonsilyl chloride in the presence of imidazole], acetalization (for example, reaction with dihydropyrane in the presence of pyridinium p-toluenesulfonate), ($C_2$-$C_{10}$)acylation (for example, reaction with an acid anhydride or an acid chloride in the presence of a base), ($C_1$-$C_{10}$)hydrocarbonsulfonylation (for example, reaction with a hydrocarbonsulfonyl chloride in the presence of a base), or a di($C_1$-$C_6$)hydrocarbonphosphorylation [for example, reaction with a di($C_1$-$C_6$)hydrogenphosphoryl chloride]. Thus, the compound of formula (III)-1 can be obtained.

As required, the protected hydroxyl group ($OR^{21}$) at the 7-position and the protected hydroxyl group ($OR^{31}$) at the 3'- (or 4'-)position of the 6-position in the compound of formula (III)-1 may be deprotected to form free hydroxyl groups.

If the protective group for the hydroxyl group is a group forming an acetal linkage together with the oxygen atom of the hydroxyl group, the deprotection can be carried out in such a reaction solvent as water, tetrahydrofuran, diethyl ether, dioxane, acetone or acetonitrile in the presence of such a catalyst as acetic acid, pyridinium p-toluenesulfonate or a cation-exchange resin. The reaction is carried out usually at a temperature of $-78°$ to $+30°$ C. for about 10 minutes to 3 days. If the protective group is a tri($C_1$-$C_7$)hydrocarbonsilyl group, the reaction is carried out in the aforesaid reaction medium at the same temperature as above for the same period of time as above in the presence of, for example, acetic acid, tetrabutylammonium fluoride, cerium fluoride, aqueous hydrogen fluoride, or pyridine-hydrogen fluoride.

The following formula (III″)

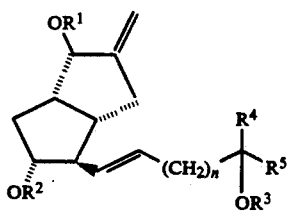

wherein $R^1$, $R^2$, $R^3$, $R^4$, $R^5$ and n are as defined hereinabove,
encompasses all of the compounds of formulae (III), (III)-1 and (III)-2.

Reaction Scheme 5

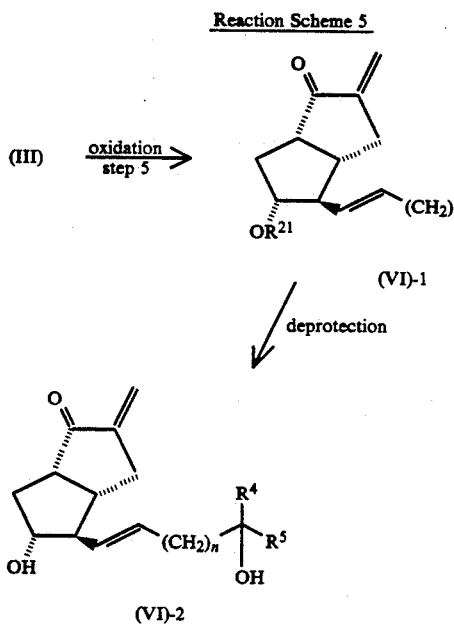

Step 5 (oxidation)

The 6,7-disubstituted-2-hydroxy-3-methylenebicyclo[3.3.0]octane of formula (III) obtained in step 3 is then reacted with an oxidizing agent for alcohol.

Examples of the oxidizing agent are manganese dioxide, chromic acid derivatives, N-halocarboximides, oxygen, 2,3-dichloro-5,6-dicyano-1,4-benzoquinone, and dimethyl disulfoxide. Of these, manganese dioxide, chromic acid derivatives (such as pyridinium dichromate), and dimethyl sulfoxide are preferred. The amount of the oxidizing agent is 0.8 to 20 moles, preferably 1.0 to 10 moles, especially preferably 1.2 to 5 moles, per mole of the 6,7-disubstituted-2-hydroxy-3-methylenebicyclo[3.3.0]octane.

The reaction temperature varies depending upon the oxidizing agent used, and is usually −78° to 120° C. The reaction time varies depending upon the reaction temperature and the kind of the oxidizing agent. Preferably, the reaction is carried out while the disappearance of the starting material is monitored by, for example, thin-layer chromatography.

The reaction is carried out in an organic medium. Examples of the organic medium are the same as those given above with regard to step 1. Other organic media such as N,N-dimethylformamide and acetone may properly be used. The amount of the organic medium is 1 to 100 times, preferably 2 to 20 times, the volume of the starting materials used.

Thus, the compound of formula (VI)-1 above is obtained. As required, the compound of formula (VI)-1 is then converted to a 6,7-disubstituted-2-oxo-3-methylenebicyclo[3.3.0]octane by deprotecting the protected hydroxyl group ($OR^{21}$) at the 7-position and the protected hydroxyl group ($OR^{21}$) at the 3′-(or 4′-)position of the 6-position to form free hydroxyl groups.

Deprotection of the protected hydroxyl group may be carried out in the same way as above.

The following formula (VI)

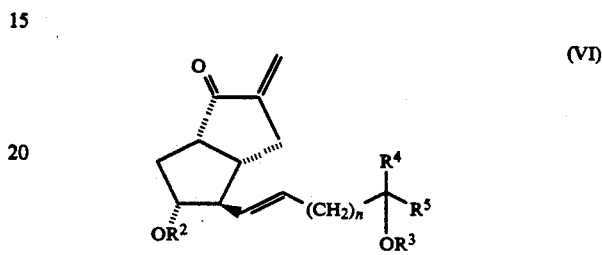

wherein $R^2$, $R^3$, $R^4$, $R^5$ and n are as defined above,
encompasses all of the compounds of formulae (VI)-1 and (VI)-2.

Formula (I) above embraces the compounds of formula (III″) and the compounds of formula (VI).

The resulting novel compounds of formula (I) are useful as novel intermediates for synthesis of isocarbacyclins, i.e. 9(0)methano-Δ$^{6(9a)}$-prostaglandins I$_1$, useful as medicines for the circulatory system such as an antithrombotic agent, an antilipidemic agent, a hypotensive agent or an antiarterosclerotic agent.

In particular, the compounds of formulae (III)-1 and (IV)-1 can be converted to useful compounds, for example, by applying the method described in J. Am. Chem. Soc., 1980, 102, 4730–4743, or Accounts of Chemical Research, 13, 385 (1980) for the compounds of formula The following examples illustrate the present invention more specifically. It should be understood, however, that the invention is in no way limited to these examples alone.

In the structural formulae given below, . . . OZ represents . . . OSiMe$_2$t—Bu, and . . . OY,

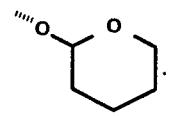

EXAMPLE 1

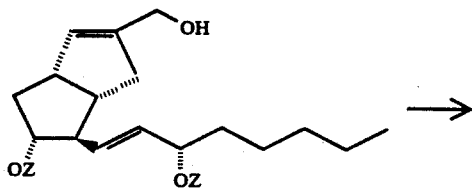

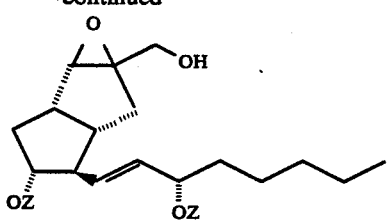

Vanadyl acetylacetonate (10 mg) was added to a solution of 1.0 g (1.97 mmoles) of (1S,5S,6S,7R)-3-hydroxymethyl-6-[(E,3S)-3-t-butyldimethylsilyloxy-1-octenyl]-7-t-butyldimethylsilyloxybicyclo[3.3.0]-2-octene in 8 ml of benzene, and 1 ml (3.0 mmoles) of a 3.0M 1,2-dichloroethane solution of anhydrous t-butyl hydroperoxide was added to the mixture at room temperature. The resulting mixture was heated under reflux for 20 minutes. The reaction mixture was cooled and concentrated. The resulting crude product was subjected to silica gel column chromatography (silica gel 50 g; hexane/ethyl acetate=6/1) to give (1S,2RS,3RS,5S,6S,7R) 3-hydroxymethyl-2,3-epoxy-6-[(E,3S)-3-t-butyldimethylsilyoxy-1-octenyl]-7-t-butyl-dimethylsilyloxybicyclo[3.3.0]octane (912 mg, 1.74 mmoles, 88

NMR(CDCl$_3$)δ: 0.04(12H,s), 0.85(21H), 1.0–1.6(8H,m), 1.6–2.7(8H,m), 3.31(1H,m), 3.67(3H,s), 3.4–4.1(2H,m), 5.15–5.35(2H,m).

IR(liquid film): 3440, 3000, 1255, 1115, 1060, 1000, 965, 860, 830, 770 cm$^{-1}$.

MS: 525(M+1), 507(M-17), 467(M-57), 449.

EXAMPLE 2

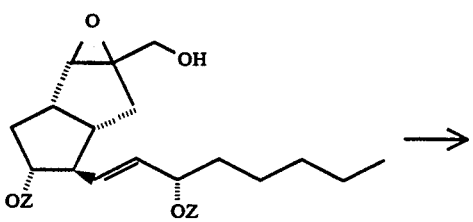

The (1S,2RS,3RS,5S,6S,7R)-3-hydroxymethyl-2,3-epoxy-6-[(E,3S)-3-t-butyldimethylsilyloxy-10-octenyl] 7-t-butyldimethylsilyloxybicyclo[3.3.0 ]octane (801 mg, 1.53 mmoles) obtained in Example 1 was dissolved in 3 ml of methylene chloride. The solution was cooled to −25° C., and then triethylamine (170 mg, 1.68 mmoles) and further a solution of methanesulfonyl chloride (193 mg, 1.68 mmoles) in 3 ml of methylene chloride were added. The mixture was stirred for 1 hour. Ice water was added to the reaction mixture, and the entire mixture was then extracted with ethyl acetate. The separated organic layer was washed with an aqueous solution of sodium chloride, dried ove anhydrous magnesium sulfate and concentrated to give (1S,2RS,3RS,5S,6S,7R)-3-methanesulfonyloxymethyl-2,3-epoxy-6-[(E,3S)-3-t-butyldimethylsilyloxybicyclo[3.30]octane (917 mg, 1.52 mmoles, 99%) as a nearly pure product.

NMR(CDCl$_3$)δ: 0.04(12H,s), 0.84(21H), 1.0–1.7(8H,m), 1.7–2.7(7H,m), 2.94(3H,s), 3.30(1H,m), 3.6–4.1(2H,m), 4.0–4.6(2H,m), 5.15–5.35(2H,m).

IR(liquid film): 3000, 1735, 1355, 1250, 1175, 1115, 1060, 1000, 960, 830, 770 cm$^{-1}$.

MS: 545(M-57), 507, 449.

EXAMPLE 3

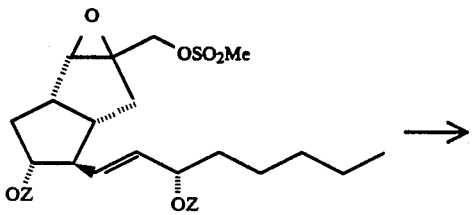

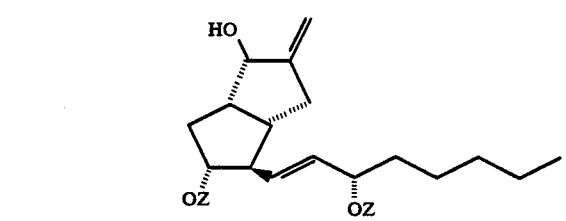

A solution of 917 mg (1.52 mmoles) of (1S,2RS,-3RS,5S,6S,7R)-3-methanesulfonyloxymethyl-2,3-epoxy-6-[(E,3S)-3-t-butyldimethylsilyloxy-1-octenyl]-7-t-butyldimethylsilyloxybicyclo[3.3.0]octane obtained in Example 2 in 3 ml of tetrahydrofuran was added to an anion radical solution prepared by reacting naphthalene (1.28 g, 10 mmoles) with sodium (207 mg, 9 mmoles) in 30 ml of tetrahydrofuran at room temperature for I hour. The mixture was stirred at room temperature for 10 minutes and 3.0 g of ammonium chloride was added to the reaction solution. Then, a saturated aqueous solution of ammonium chloride was added and the resulting mixture was extracted with ethyl acetate. The organic layer was washed with an aqueous solution of sodium chloride, dried over anhydrous magnesium sulfate and concentrated to give a crude product. It was subjected to column chromatography (silica gel 50 g; hexane/ethyl acetate=19/1) to give (1S,2RS,5S,-6S,7R)-2-hydroxy-3-methylene-6-[(E,3S)-3-t-butyldimethyl-silyloxy- 1-octenyl) -7-t-butyldimethylsilyloxybicyclo[3.3.0]octane (605 mg, 1.19 mmoles, 78%).

NMR(CDCl$_3$)δ: 0.05(12H,s), 0.85(21H), 1.0–3.0(16H,m), 3.4–4.5(3H,m), 4.7–5.1(2H,m), 5.2–5.35(2H,m).

IR(liquid film): 3350, 3080, 1660, 1255, 1115, 1000, 965, 935, 835, 770 cm$^{-1}$.

MS: 508(M+), 491(M-17), 451(M-57).

EXAMPLE 4

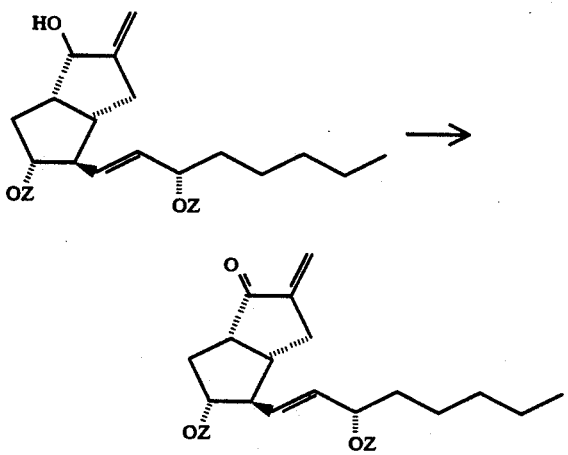

The (1S,3RS,5S,6S,7R)-2-hydroxy-3-methylene-6-[(E,3S)-3-t-butyldimethylsilyloxy-1-octenyl]-7-t-butyl-dimethylsilyloxybicyclo[3.3.0]octane (150 mg, 0.295 mmole) obtained in Example 3 was dissolved in 3 ml of N,N-dimethylformamide, and 147 mg (9.39 mmole) of pyridinium dichromate was added at 0° C. the mixture was stirred for 5 hours. The reaction mixture was added to water, and extracted with hexane. The resulting organic layer was washed with an aqueous solution of sodium chloride, dried over anhydrous magnesium sulfate, and concentrated to give 156 g of a crude product. The product was subjected to column chromatography (silica gel 30 g, hexane/ethyl acetate=19/1) to yield (1S,5S,6S,7R)-2-oxo-3-methylene-6-[(E,3S)-3-t-butyl-dimethylsilyloxy-1-octenyl]w7-t-butyldimethylsilylox-ybicyclo[3.3.0]octane (102 mg, 0.20 mmole, 68%).

NMR(CDCl$_3$)δ: 0.04(12H,s), 0.86(21H), 1.0-2.8(15H,m), 3.5-4.2(2H,m), 5.16(1H,m), 5.2-5.5(2H,m), 5.83(1H,m).

IR(liquid film): 1725, 1640, 1255, 1115, 1070, 835, 770 cm$^{-1}$.

MS: 506(M+) 449(M-57).

EXAMPLE 5

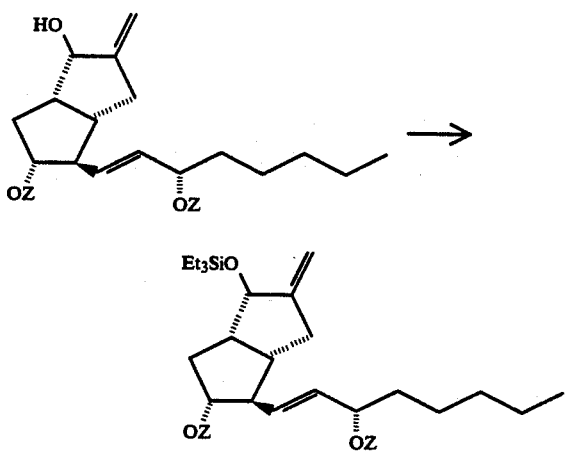

The (1S,2RS,5S,6S,7R)-2-hydroxy-3-methylene-6-[(E,3S)-3-t-butyldimethylsilyloxy-1-octenyl]-7-butyl-dimethylsilyloxybicyclo[3.3.0]octane (102 mg, 0.20 mmole) obtained in Example 3 was dissolved in 1 ml of N,N-dimethylformamide, and triethylsilyl chloride (45 mg, 0.30 mmole) and imidazole (34 mg, 0.50 mmole) were added, and the mixture was stirred at room temperature for 3 hours. Ice water was added to the reaction mixture, and the mixture was extracted with hexane. The resulting organic layer was dried over anhydrous magnesium sulfate, and concentrated. The resulting crude product was subjected to column chromatography (silica gel 10 g; hexane/ethyl acetate=49/1) to give (1S,2RS,5S,6S,7R)-2-triethylsilyloxy-3-methylene-6[(E,3S)-3-t-butyldimethylsilyloxy-1-octenyl]-7-t-butyl-dimethylsilyloxybicyclo[3.3.0]octane (112 mg, 0.18 mmole, 90%).

NMR(CDCl$_3$)δ: 0.05(12H,s), 0.57(6H,m), 0.85(21H), 0.8-3.0(24H,m), 3.4-4.5(3H,m), 4.7-5.1(2H,m), 5.2-5.35(2H,m).

IR(liquid film): 3080, 1660, 1255, 1115, 1000, 965, 935, 835, 770 cm$^{-1}$.

MS: 622(M+), 565(M-57).

EXAMPLE 6

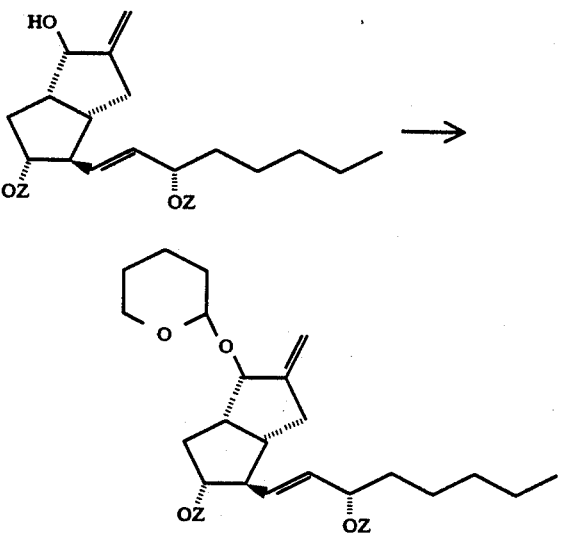

(1S,2RS,5S,6S,7R)-2-hydroxy-3-methylene-6-[(E,3S)-3-t-butyldimethylsilyloxy-1-octenyl]-7-t-butyl-dimethylsilyloxybicyclo[3.3.0]octane (127 mg, 0.25 mmole) obained in Example 3 was dissolved in 2 ml of methylene chloride. Dihydropyrane (42 mg, 0.50 mmole) and pyridium p-toluenesulfonate (5 mg) were added to the solution, and the mixture was stirred at room temperature for 8 hours. Water and methylene chloride were added to the reaction mixture to perform extraction. The resulting organic layer was washed with an aqueous solution of sodium chloride, dried over anhydrous magnesium sulfate and concentrated. The resulting crude product was subjected to column chromatography (silica gel 15 g, hexane/ethyl acetate=30/1) to give (1S,2RS,5S,6S,7R)-2-(2-tetrahy-dropyranyloxy)-3-methylene-6-[(E,3S)-3-t-butyldime-thylsilyloxy-1-octenyl]-7-t-butyl-7-t-butyldimethyl-silyloxybicyclo[3.3.0]octane (130 mg, 0.22 mmole, 88%).

NMR(CDCl$_3$)δ: 0.05(12H,s), 0.84(21H), 1.0-3.0(21H,m), 3.2-4.5(5H,m), 4.4-4.7(1H,m), 4.7-5.1(2H,m), 5.2-5.35(2H,m).

IR(liquid film): 3080, 1660, 1255, 1115, 1000, 965, 935, 835, 770 cm$^{-1}$.

MS: 592(M+), 535(M-57).

EXAMPLE 7

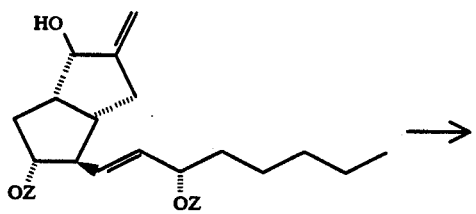

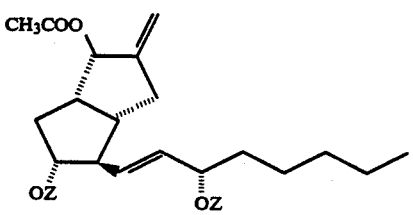

Acetic anhydride (0.5 ml) and pyridine (0.5 ml) were added to 95 mg (0.187 mmole) of (1S,2RS,5S,6S,7R)-2-hydroxy-3-methylene-6-[(E,3S)-3-t-butyldimethyl-silyloxy-1-octenyl]-7-t-butyldimethylsilyloxybicyclo[3.3.0]octane obtained in Example 3, and the mixture was stirred at room temperature for 10 hours. The reaction mixture was concentrated under reduced pressure, and then subjected to column chromatography (silica gel 20 g, hexane/ethyl acetate=19/1) to give (1S,2RS,5S,6S,7R)-2-acetoxy-3-methylene-6-[(E,3S)-3-t-butyldimethylsilyloxy-1-octenyl]-7-t-butyldimethylsilyloxybicyclo[3.3.0]octane (101 mg, 0.184 mmole, 98%).

NMR(CDCl$_1$ )δ: 0.05(12H,s), 0.84(21H), 1.0–2.8(15H,m), 1.95 (3H,s), 3.4–4.1 (3H,m) , 4.8–5.1(2H,m), 5.2–5.4(2H,m).

IR(liquid film): 3080, 1740, 1660, 1250, 1235, 1120, 965, 855, 835, 775 cm$^{-1}$.

MS: 550(M+), 493(M-57), 490.

EXAMPLE 8

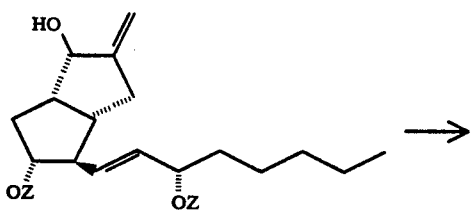

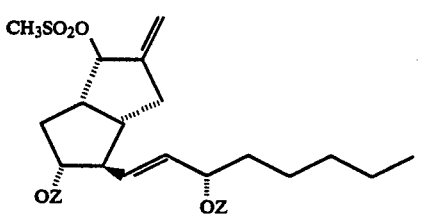

The (1S,2RS,5S,6S,7R)-2-hydroxy-3-methylene-6-[(E,3S)-3-t-butyldimethylsilyloxy-1-octenyl]-7-t-butyl-dimethylsilyloxybicyclo[3.3.0]octane (127 mg, 0.25 mmole) obtained in Example 3 was dissolved in 1 ml of methylene chloride. The solution was cooled to −25° C., and triethylamine (38 mg, 0.375 mmole) and then a solution of methanesulfonyl chloride (43 mg, 0.375 mmole) in 1 ml of methylene chloride were added. The mixture was stirred for 2 hours. Ice water was added to the reaction mixture, and the mixture was extracted with ethyl acetate. The separated organic layer was washed with an aqueous solution of sodium chloride, dried over anhydrous magnesium sulfate, and concentrated. The crude product was subjected to column chromatography (silica gel 15 g; hexane/ethyl acetate=30/1) to give (1S,2RS,5S,6S,7R)-2-methanesulfonyloxy-3-methylene-6-[(E,3S)-3-t-butyldimethyl-silyloxy-1-octenyl]-7-t-butyldimethylsilyloxybicyclo[3.3.0]octane (123 mg, 0.21 mmole, 84%).

NMR(CDCl$_1$ )δ: 0.05(12H,s), 0.85(21H), 1.0–3.0(15H,m), 2.93(3H,s), 3.4–4.5(3H,m), 4.7–5.1(2H,m), 5.2–5.35(2H,m).

IR(liquid film): 3080, 1735, 1660, 1355, 1255, 1115, 1000, 960, 830, 770 cm$^{-1}$.

MS: 586(M+), 529(M-57), 490.

EXAMPLE 9

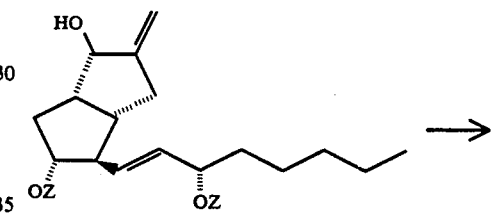

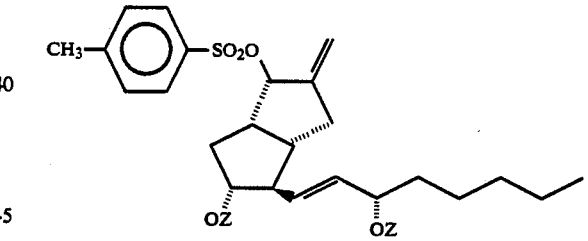

In the same way as in Example 8, (1S,2RS,5S,6S,7R)-2-hydroxy-3-methylene-6-[(E,3S)-3-t-butyldimethyl-silyloxy- 1-octenyl]-7-t-butyldinmethylsilyloxybicyclo[3.3.0]octane (178 mg, 0.35 mmole) obtained in Example 3 was reacted with p-toluenesulfonyl chloride (133 mg, 0.70 mmole). The reaction mixture was worked up and column-chromatographed to give (1S,2RS,5S,6S,7R)-2-p-toluenesulfonyloxy-3-methylene-6-[(E,3S)-3-t-butyldimethylsilyloxy-1-octenyl]-7-t-butyldimethylsilyloxybicyclo[3.3.0]octane (179 mg, 0.27 mmole, 78%).

NMR(CDCl$_1$ )δ: 0.05(12H,s), 0.85(21H), 1.0–3.0(15H,m), 2.33(3H,s), 3.4–4.5(3H,m), 4.7–5.1(2H,m), 5.2–5.35(2H,m). 7.13(2H,d,J=9 Hz), 7.60(2H,d,J=9 Hz).

IR(liquid film): 3080, 1660, 1600, 1355, 1255, 1175, 1115, 1000, 965, 935, 700 cm$^{-1}$.

MS: 662(M+), 605(M-57), 507.

EXAMPLE 10

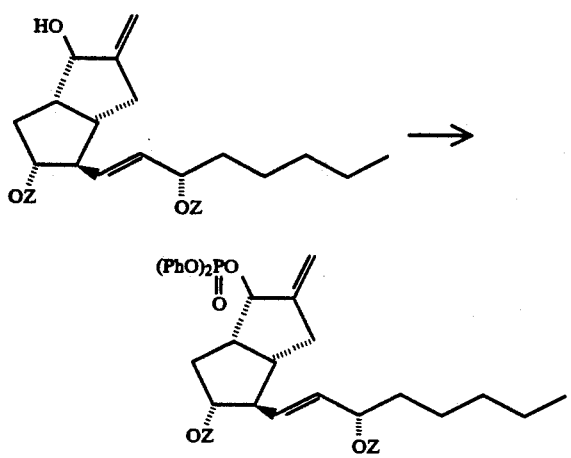

(1S,2RS,5S,6S,7R)-2-hydroxy-3-methnylene-6-[(E,2S)-3-t-butyldimethylsilyloxy-1-octenyl]-7-t-butyldimethylsilyloxybicyclo[3.3.0]octane (102 mg, 0.20 mmole) obtained in Example 3 was dissolved in 1 ml of methylene chloride. Diphenylphosphoryl chloride (81 mg, 0.30 mmole) and triethylamine (51 mg, 0.50 mmole) were added to the solution, and the mixture was stirred at room temperature for 18 hours. Ice water was added to the reaction mixture, and the mixture was extracted with ethyl acetate. The separated organic layer was washed with an aqueous solution of sodium chloride, dried over anhydrous magnesium sulfate, and concentrated. The crude product was subjected to column chromatography (silica gel 20 g; hexane/ethyl acetate=20/1) to give (1S,2RS,5S,6S,7R)-2-diphenylphosphoryl-oxy-3-methylene-6-[(E,3S)-3-t-butyldimethyl silyloxy-1-octenyl]-7-t-butyldimethylsilyloxybicyclo[3.3.0]octane (104 mg, 0.14 mmole, 70%).

NMR(CDCl$_3$)δ: 0.05(12H,s), 0.85(21H), 1.0–3.0(15H,m), 3.4–4.5(3H,m), 4.7–5.1(2H,m), 5.2–5.35(2H,m). 7.30 (10H, s) .

IR(liquid film): 3080, 1660, 1590, 1255, 1190, 1115, 1050, 1000, 965, 935, 835, 770 cm$^{-1}$.

MS: 683(M-57), 647, 507.

EXAMPLES 11–18

By the same way as in Example 1, the following compounds were synthesized.

EXAMPLE 11

(1S,2RS,3RS,5S,6S,7R)-3-hydroxymethyl-2,3-epoxy-6-[(E,3S,5R)-3-t-butyldimethylsilyloxy-5-methyl-1-nonenyl]-7-t-butyldimethylsilyloxybicyclo[3.3.0]octane (90%).

EXAMPLE 12

(1S,2RS,3RS,5S,6S,7R)-3-hydroxymethyl-2,3-epoxy-6-[(E,3S,5S)-3-t-butyldimethylsilyloxy-5-methyl-1-nonenyl]-7-t-butyldimethylsilyloxybicyclo[3.3.0]octane (90%).

EXAMPLE 13

(1S,2RS,3RS,5S,6S,7R)-3-hydroxymethyl-2,3-epoxy-6-[(E,3S)-3-t-butyldimethylsilyloxy-3-cyclopentyl-1-propenyl]-7-t-butyldimethylsilyloxybicyclo[3.3.0]octane (86%).

EXAMPLE 14

(1S,2RS,3RS,5S,6S,7R)-3-hydroxymethyl-2,3-epoxy-6-[(E,3S)-3-butyldimethylsilyloxy-3-cyclohexyl-1-propenyl]-7-t-butyldimethylsilyloxybicyclo[3.3.0]octane (85%).

EXAMPLE 15

(1S,2RS,3RS,5S,6S,7R)-3-hydroxymethyl-2,3-epoxy-6-[(E)-4-t-butyldimethylsilyloxy-4-methyl-1-octenyl]7-t-butyldimethylsilyloxybicyclo[3.3.0]octane (83%).

EXAMPLE 16

(1S,2RS,3RS,5S,6S,7R)-3-hydroxymethyl-2,3-epoxy-6-[(E)-4-t-butyldimethylsilyloxy-4-vinyl-1-octenyl]-7-t-butyldimethylsilyloxybicyclo[3.3.0]octane (89%).

EXAMPLE 17

(1S,2RS,3RS,5S,6S,7R)-3-hydroxymethyl-2,3-epoxy-6-[(E)-3-t-butyldimethylsilyloxy-3-methyl-1-octenyl]-7-t-butyldimethylsilyloxybicyclo[3.3.0]octane (83%).

EXAMPLE 18

(1S,2RS,3RS,5S,6S,7R)-3-hydroxymethyl-2,3-epoxy-6-[(E)-3-t-butyldimethylsilyloxy-4,4-dimethyl-1-octenyl]7-t-butyldimethylsilyloxybicyclo[3.3.0]octane (91%).

The characteristic spectral data of these compounds are listed in Table 1.

EXAMPLES 19–26

In the same way as in Example 2, the following compounds were synthesized.

EXAMPLE 19

(1S,2RS,3RS,5S,6S,7R)-3-methanesulfonyloxymethyl-2,3-epoxy-6-[E,3S,5R)-3-t-butyldimethylsilyloxy-5-methyl-1-nonenyl]-7-t-butyldimethylsilyloxybicyclo[3.3.0]octane (97%).

EXAMPLE 20

(1S,2RS,3RS,5S,6S,7R)-3-methanesulfonyloxymethyl-2,3-epoxy-6-[(E,3S,5S)-3-t-butyldimethylsilyloxy-5-methyl-1-nonenyl]-7-t-butyldimethylsilyloxybicyclo[3.3.0]octane (92%).

EXAMPLE 21

(1S,2RS,3RS,5S,6S,7R)-3-methanesulfonyloxymethyl-2,3-epoxy-6-[(E,3S)-3-t-butyldimethylsilyloxy-3-cyclopentyl-1-propenyl]-7-t-butyldimethylsilyloxybicyclo[3.3.0]octane (96%).

EXAMPLE 22

(1S,2RS,3RS,5S,6S,7R)-3-methanesulfonyloxymethyl-2,3-epoxy-6[(E,3S)-3-t-butyldimethylsilyloxy-3-cyclohexyl-1-propenyl]-7-t-butyldimethylsilyloxybicyclo[3.3.0]octane (93%).

EXAMPLE 23

(1S,2RS,3RS,5S,6S,7R)-3-methanesulfonyloxymethyl-2,3-epoxy-6-[(E)-4-t-butyldimethylsilyloxy-4-methyl-1-octenyl]-7-t-butyldimethylsilyloxybicyclo[3.3.-0]octane (89%).

EXAMPLE 24

(1S,2RS,3RS,5S,6S,7R)-3-methanesulfonyloxymethyl-2,3-epoxy-6-[(E)-4-t-butyldimethylsilyloxy-4-vinyl- 1-octenyl]-7-butyldimethylsilyloxybicyclo[3.3.0]octane (98%).

EXAMPLE 25

(1S,2RS,3RS,5S,6S,7R)-3-methanesulfonyloxymethyl-2,3-epoxy-6-[(E)-3-t-butyldimethylsilyloxy-3-methyl-1-octenyl]-7-t-butyldimethylsilyloxybicyclo[3.3.01 octane (93%).

EXAMPLE 26

(1S,2RS,3RS,5S,6S,7R)-3-methanesulfonyloxymethyl-2,3-epoxy-6-[(E)-3-t-butyldimethylsilyloxy-4,4-dimethyl-octenyl]-7-t-butyldimethylsilyloxybicyclo[3,3,0]octane (95%).

The characteristic spectral data of these compounds are listed in Table 2.

EXAMPLES 27-34

In the same way as in Example 3, the following compounds were synthesized.

EXAMPLE 27

(1S,2RS,3RS,5S,6S,7R)-2-hydroxy-3-methylene-6-[(E,3S,5R)-3-t-butyldimethylsilyloxy-5-methyl-1-nonenyl]7-t-butyldimethylsilyloxybicyclo[3.3.0]octane (76%).

EXAMPLE 28

(1S,2RS,3RS,5S,6S,7R)-2-hydroxy-3-methylene-6-[(E,3S,5S)-3-t-butyldimethylsilyloxy-5-methyl-1-nonenyl]-7-t-butyldimethylsilyloxybicyclo[3.3.0]octane (76%).

EXAMPLE 29

(1S,2RS,3RS,5S,6S,7R)-2-hydroxy-3-methylene-6-[(E,3S)-3-t-butyldimethylsilyloxy-3-cyclopentyl-1-propenyl]-7-t-butyldimethylsilyloxybicyclo[3.3.0]octane (72%).

EXAMPLE 30

(1S,2RS,3RS,5S,6S,7R)-2-hydroxy-3-methylene-6-[(E,3S)-3-t-butyldimethylsilyloxy-3-cyclohexyl-1-propenyl]-7-t-butyldimethylsilyloxybicyclo[3.3.0loctane (71%).

EXAMPLE 31

(1S,2RS,3RS,5S,6S,7S)-2-hydroxy-3-methylene-6-[(E)-4-butyldimethylsilyloxy-4-methyl-1-octenyl]-7-t-butyldimethylsilyloxybicyclo[3.3.0]octane (69%).

EXAMPLE 32

(1S,2RS,3RS,5S,6S,7R)-2-hydroxy-3-methylene-6-[(E)-4-t-butyldimethylsilyloxy-4-vinyl-1-octenyl]-7-t-butyldimethylsilyloxybicyclo[3.3.0]octane (74%).

EXAMPLE 33

(1S,2RS,3RS,5S,6S,7R)-2-hydroxy-3-methylene-6-[(E)-3-t-butyldimethylsilyloxy-3-methyl-1-octenyl]-7-t-butyldimethylsilyloxybicyclo[3.3.0]octane (63%).

EXAMPLE 34

(1S,2RS,3RS,5S,6S,7R)-2-hydroxy-3-methylene-6-[(E)-3-t-butyldimethylsilyloxy-4,4-dimethyl-1-octenyl]7-t-butyldimethylsilyloxybicyclo[3.3.0]octane (70%).

The characteristic spectral data of these compounds are listed in Table 3.

EXAMPLES 35-42

In the same way as in Example 4, the following compounds were synthesized.

EXAMPLE 35

(1S,2RS,3RS,5S,6S,7R)-2-oxo-3-methylene-6-[(E,3S,5R)-3-t-butyldimethylsilyl-5-methyl-1-nonenyl]-7-t-butyldimethylsilyloxybicyclo[3.3.0]octane (62%).

EXAMPLE 36

(1S,2RS,3RS,5S,6S,7R)-2-oxo-3-methylene-6-[(E,3S,5S)-3-t-butyldimethylsilyloxy-5-methyl-1-nonenyl]-7-t-butyldimethylsilyloxybicyclo[3.3.0]octane (71%).

EXAMPLE 37

(1S,2RS,3RS,5S,6S,7R)-2-oxo-3-methylene-6-[(E,3S)-3-t-butyldimethylsilyloxy-3-cyclopentyl-1-propenyl]-7-t-butyldimethylsilyloxybicyclo[3.3.0]octane (64%).

EXAMPLE 38

(1S,2RS,3RS,5S,6S,7R)-2-oxo-3-methylene-6-[(E,3S)-3-t-butyldimethylsilyloxy-3-cyclohexyl-1-propenyl]-7-t-butyldimethylsilyloxybicyclo[3.3.0]octane (69%).

EXAMPLE 39

(1S,2RS,3RS,5S,6S,7R)-2-oxo-3-methylene-6-[(E)-4-t-butyldimethylsilyloxy-4-methyl-1-octenyl]-7-t-butyldimethylsilyloxybicyclo[3.3.0]octane (65%).

EXAMPLE 40

(1S,2RS,3RS,5S,6S,7R)-2-oxo-3-methylene-6-[(E)-4-t-butyldimethylsilyloxy-4-vinyl-1-octenyl]-7-t-butyldimethylsilyloxybicyclo[3.3.0]octane (69%).

EXAMPLE 41

(1S,2RS,3RS,5S,6S,7R)-2-oxo-3-methylene-6-[(E)-3-t-butyldimethylsilyloxy-3-methyl-1-octenyl]-7-t-butyldimethylsilyloxybicyclo[3.3.0]octane (63%).

EXAMPLE 42

(1S,2RS,3RS,5S,6S,7R)-2-oxo-3-methylene-6-[(E)-3-t-butyldimethylsilyloxy-4,4-dimethyl-1-octenyl]-6-t-butyldimethylsilyloxybicyclo[3.3.0]octane (61%).

EXAMPLES 43-50

In the same way as in Example 7, the following compounds were synthesized.

EXAMPLE 43

(1S,2RS,3RS,5S,6S,7R)-2-acetoxy-3-methylene-6-[(E,3S,5R)-3-t-butyldimethylsilyloxy-5-methyl-1-nonenyl]-7-t-butyldimethylsilyloxybicyclo[3.3.0]octane (99%).

EXAMPLE 44

(1S,2RS,3RS,5S,6S,7R)-2-acetoxy-3-methylene-6-[(E,3S,5S)-3-t-butyldimethylsilyloxy-5-methyl-1-nonenyl]-7-t-butyldimethylsilyloxybicyclo[3.3.0]octane (99%).

EXAMPLE 45

(1S,2RS,3RS,5S,6S,7R)-2-acetoxy-3-methylene-6-[(E,3S)-3-t-butyldimethylsilyloxy-3-cyclopentyl-1- propenyl]-7-t-butyldimethylsilyloxybicyclo[3.3.0]octane (98%).

EXAMPLE 46

(1S,2RS,3RS,5S,6S,7R)-2-acetoxy-3-methylene-6-[(E,3S)-3-t-butyldimethylsilyloxy-3-cyclohexyl-1-propenyl]-7-t-butyldimethylsilyloxybicyclo[3.3.0]octane (99%).

EXAMPLE 47

(1S,2RS,3RS,5S,6S,7R)-2-acetoxy-3-methylene-6-[(E)-4-t-butyldimethylsilyloxy-4-methyl-1-octenyl]-7-t-butyldimethylsilyloxybicyclo[3.3.0]octane (97%).

EXAMPLE 48

(1S,2RS,3RS,5S,6S,7R)-2-acetoxy-3-methylene-6-[(E)-4-t-butyldimethylsilyloxy-4-vinyl-1-octenyl]-7-t-butyldimethylsilyloxybicyclo[3.3.0]octane (99%).

EXAMPLE 49

(1S,2RS,3RS,5S,6S,7R)-2-acetoxy-3-methylene-6-[(E)-3-t-butyldimethylsilyloxy-3-methyl-1-octenyl]-7-t-butyldimethylsilyloxybicyclo[3.3.0]octane (98%).

EXAMPLE 50

(1S,2RS,3RS,5S,6S,7R)-2-acetoxy-3-methylene-6-[(E)-3-t-butyldimethylsilyloxy-4,4-dimethyl-1-octenyl]-7-t-butyldimethylsilyloxybicyclo[3.3.0]octane (96%).

The characterisic spectral data of these compounds are listed in Table 5.

EXAMPLES 51-54

In the same way as in Example 8, the following compounds were synthesized.

EXAMPLE 51

(1S,2RS,3RS,5S,6S,7R)-2-methanesulfonyloxy-3-methylene-6-[(E,3S,5R)-3-t-butyldimethylsilyloxy-5-methyl-1-nonenyl]-7-t-butyldimethylsilyloxybicyclo[3.3.0]octane (81%).

EXAMPLE 52

(1S,2RS,3RS,5S,6S,7R)-2-methanesulfonyloxy-3-methylene-6-[(E,3S,5S)-3-t-butyldimethylsilyloxy-5-methyl-1-nonenyl]-7-t-butyldimethylsilyloxybicyclo[3.3.0]octane (83%).

EXAMPLE 53

(1S,2RS,3RS,5S,6S,7R)-2-methanesulfonyloxy-3-methylene-6-[(E,3S)-3-t-butyldimethylsilyloxy-3-cyclopentyl-1-propenyl]-7-t-butyldimethylsilyloxybicyclo[3.3.0]octane (81%).

EXAMPLE 54

(1S,2RS,3RS,5S,6S,7R)-2-methanesulfonyloxy-3-methylene-6-[(E)-4-t-butyldimethylsilyloxy-4-methyl-1-octenyl]-7-t-butyldimethylsilyloxybicyclo[3.3.0]octane (79%).

The characteristic spectral data of these compounds are listed in Table 9.

EXAMPLES 55-58

In the same way as in Example 9, the following compounds were synthesized.

EXAMPLE 55

(1S,2RS,3RS,5S,6S,7R)-2-p-toluenesulfonyloxy-3-methylene-6-[(E,3S,5R)-3-t-butyldimethylsilyloxy-5-methyl-1-nonenyl]-7-t-butyldimethylsilyloxybicyclo[3.3.0]octane (73%).

EXAMPLE 56

(1S,2RS,3RS,5S,6S,7R)-2-p-toluenesulfonyloxy-3-methylene-6-[(E,3S,5S)-3-t-butyldimethylsilyloxy-5-methyl-1-nonenyl]-7-t-butyldimethylsilyloxybicyclo[3.3.0]octane (79%).

EXAMPLE 57

(1S,2RS,3RS,5S,6S,7R)-2-p-toluenesulfonyloxy-3-methylene-6-[(E,3S)-3-t-butyldimethylsilyloxy-3-cyclopentyl-1-propenyl]-7-t-butyldimethylsilyloxybicyclo[3.3.0]octane (69%).

EXAMPLE 58

(1S,2RS,3RS,5S,6S,7R)-2-p-toluenesulfonyloxy-3-methylene-6-[(E)-4-t-butyldimethylsilyloxy-4-methyl-1-octenyl]-7-t-butyldimethylsilyloxybicyclo[3.3.0]octane (76%).

The characteristic spectral data of these compounds are listed in Table 7.

EXAMPLES 59-62

In the same way as in Example 10, the following compounds were synthesized.

EXAMPLE 59

(1S,2RS,3RS,5S,6S,7R)-2-diphenylphosphoryloxy-3-methylene-6-[(E,3S,5R)-3-t-butyldimethylsilyloxy-5-methyl-1-nonenyl]-7-t-butyldimethylsilyloxybicyclo[3.3.0]octane (72%).

EXAMPLE 60

(1S,2RS,3RS,5S,6S,7R)-2-diphenylphosphoryloxy-3-methylene-6-[(E,3S,5S)-3-t-butyldimethylsilyloxy-5-methyl-1-nonenyl]-7-t-butyldimethylsilyloxybicyclo[3.3.0]octane (69%).

EXAMPLE 61

(1S,2RS,3RS,5S,6S,7R)-2-diphenylphosphoryloxy-3-methylene-6-[(E,3S)-3-t-butyldimethylsilyloxy-3-cyclopentyl-1-propenyl]-7-t-butyldimethylsilyloxybicyclo]3.3.0]octane (67%).

EXAMPLE 62

(1S,2RS,3RS,5S,6S,7R)-2-diphenylphosphoryloxy-3-methylene-6-[(E)-4-t-butyldimethylsilyloxy-4-methyl-1-octenyl]-7-t-butyldimethylsilyloxybicyclo[3.3.0]octane (83%).

The characteristic spectral data of these compounds are listed in Table 8.

TABLE 1

| | 3-hydroxymethyl-2,3-epoxybicyclo[3.3.0]octanes | | |
|---|---|---|---|
| Example | $^1$H NMR (CDCl$_3$, δ (ppm)) | IR (liquid film, cm$^{-1}$) | MS |
| 11 | 0.03(12H, s), 0.85(24H), 1.0–1.6(9H, m), 1.6–2.7(8H, m), 3.31(1H, m), 3.67(2H, s), 3.4–4.1(2H, m), 5.15–5.35(2H, m). | 3420, 1255, 1115, 1060, 835, 770. | 553 (M+1), 535 (M−17), 495 (M−57). |
| 12 | 0.03(12H, s), 0.85(24H), 1.0–1.6(9H, m), 1.6–2.7(8H, m), 331(1H, m), 3.67(2H, s), 3.4–4.1(2H, m), 5.15–5.35(2H, m). | 3420, 1255, 1115, 1060, 835, 770. | 553 (M+1), 535 (M−17), 495 (M−57). |

TABLE 1-continued

3-hydroxymethyl-2,3-epoxybicyclo[3.3.0]octanes

| Example | $^1$H NMR (CDCl$_3$, δ (ppm)) | IR (liquid film, cm$^{-1}$) | MS |
|---|---|---|---|
| 13 | 0.03(12H, s), 0.85(18H, s), 1.0-1.6(9H, m), 1.6-2.7(8H, m), 3.30(1H, m), 3.67(2H, s), 3.42-4.2(2H, m), 5.15-5.35(2H, m). | 3400, 1255, 1115, 1060, 835, 770. | 523 (M+1), 505 (M−17), 465 (M−57). |
| 14 | 0.03(12H, s), 0.85(18H, s), 1.0-1.6(11H, m), 1.6-2.7(8H, m), 3.30(1H, m), 3.67(2H, s), 3.4-4.2(2H, m), 5.15-5.35(2H, m). | 3430, 1255, 1115, 1060, 835, 770. | 537 (M+1), 519 (M−17), 479 (M−57). |
| 15 | 0.03(12H, s), 0.85(21H), 1.11(3H, s), 1.0-2.7(16H, m), 3.30(1H, m), 3.66(2H, s), 3.4-4.2(1H, m), 5.15-5.35(2H, m). | 3420, 1255, 1115, 1060, 835, 770. | 539 (M+1), 521 (M−17), 481 (M−57). |
| 16 | 0.03(12H, s), 0.85(21H), 1.0-2.7(16H, m), 3.31(1H, m), 3.67(2H, s), 3.4-4.2(1H, m), 4.7-5.4(5H, m). | 3440, 1255, 1115, 1060, 835, 770. | 551 (M+1), 533 (M−17), 493 (M−57). |
| 17 | 0.03(12H, s), 0.85(21H), 1.0-1.6(8H, m), 1.20(3H, s), 1.6-2.7(8H, m), 3.31(1H, m), 3.67(2H, s), 3.4-4.1(1H, m), 5.2-5.4(2H, m). | 3420, 1255, 1115, 1060, 835, 770. | 539 (M+1), 521 (M−17), 481 (M−57). |
| 18 | 0.04(12H, s), 0.85(21H), 1.13(6H, s), 1.0-1.6(6H, m), 1.6-2.7(8H, m), 3.31(1H, m), 3.67(2H, s), 3.4-4.1(2H, m), 5.2-5.4(2H, m). | 3430, 1255, 1115, 1060, 835, 770. | 553 (M+1), 535 (M−17), 495 (M−57). |

TABLE 2

3-methanesulfonyloxymethyl-2,3-epoxybicyclo-[3.3.0]octanes

| Example | $^1$H NMR (CDCl$_3$, δ (ppm)) | IR (liquid film, cm$^{-1}$) | MS |
|---|---|---|---|
| 19 | 0.04(12H, s), 0.84(24H), 1.0-1.7(9H, m), 1.7-2.7(7H, m), 2.93(3H, s), 3.30(1H, m), 3.6-4.1(2H, m), 4.0-4.6(2H, m), 5.15-5.35(2H, m). | 1355, 1250, 1175, 1115, 965, 830, 770. | 573 (M−57). |
| 20 | 0.04(12H, s), 0.84(24H), 1.0-1.7(9H, m), 1.7-2.7(7H, m), 2.93(3H, s), 3.30(1H, m), 3.6-4.1(2H, m), 4.0-4.6(2H, m), 5.15-5.35(2H, m). | 1355, 1250, 1175, 1115, 965, 830, 770. | 573 (M−57). |
| 21 | 0.03(12H, s), 0.85(18H), 1.0-1.7(9H, m), 1.7-2.7(7H, m), 2.93(3H, s), 3.30(1H, m), 3.6-4.1(2H, m), 4.0-4.6(2H, m), 5.15-5.35(2H, m). | 1355, 1250, 1175, 1115, 965, 830, 770. | 543 (M−57). |
| 22 | 0.03(12H, s), 0.85(18H), 1.0-1.7(11H, m), 1.7-2.7(7H, m), 2.93(3H, s), 3.31(1H, m), 3.6-4.1(2H, m), 4.0-4.6(2H, m), 5.15-5.35(2H, m). | 1355, 1250, 1175, 1115, 965, 830, 770. | 557 (M−57). |
| 23 | 0.04(12H, s), 0.85(21H), 1.11(3H, s), 1.0-2.7(15H, m), 2.93(3H, s), 3.30(1H, m), 3.6-4.1(2H, m), 4.0-4.6(2H, m), 5.15-5.35(2H, m). | 1355, 1250, 1175, 1115, 965, 830, 770. | 559 (M−57). |
| 24 | 0.03(12H, s), 0.85(21H), 1.0-2.7(15H, m), 2.93(3H, s), 3.31(1H, m), 3.6-4.1(2H, m), 4.0-4.6(2H, m), 4.7-5.4(2H, m). | 1355, 1250, 1175, 1115, 970, 835, 770. | 571 (M−57). |
| 25 | 0.03(12H, s), 0.84(21H), 1.0-1.6(8H, m), 1.20(3H, s), 1.6-2.7(7H, m), 2.93(3H, s), 3.30(1H, m), 3.6-4.1(2H, m), 4.0-4.6(2H, m), 5.15-5.35(2H, m). | 1355, 1250, 1175, 1115, 970, 835, 770. | 559 (M−57). |
| 26 | 0.03(12H, s), 0.84(21H), 1.0-1.7(6H, m), 1.13(6H, s), 1.7-2.7(7H, m), 2.93(3H, s), 3.30(1H, m), 3.6-4.1(2H, m), 4.0-4.6(2H, m), 5.15-5.35(2H, m). | 1355, 1250, 1175, 1115, 965, 830, 770. | 573 (M−57). |

TABLE 3

2-hydroxy-3-methylenebicyclo[3.3.0]octanes

| Example | $^1$H NMR (CDCl$_3$, δ (ppm)) | IR (liquid film, cm$^{-1}$) | MS |
|---|---|---|---|
| 27 | 0.05(12H, s), 0.85(24H), 1.0-3.0(17H, m), 3.4-4.5(3H, m), 4.7-5.1(2H, m), 5.2-5.35(2H, m). | 3420, 3080, 1255, 1110, 835, 770. | 536 (M$^+$), 519 (M−17), 479 (M−57). |
| 28 | 0.05(12H, s), 0.85(24H), 1.0-3.0(17H, m), 3.4-4.5(3H, m), 4.7-5.1(2H, m), 5.2-5.35(2H, m). | 3420, 3080, 1255, 1110, 835, 770. | 536(M$^+$), 519 (M−17), 479 (M−57). |
| 29 | 0.04(12H, s), 0.84(18H), 1.0-3.0(17H, m), 3.4-4.5(3H, m), 4.7-5.1(2H, m), 5.2-5.35(2H, m). | 3420, 3080, 1255, 1110, 835, 770. | 506(M$^+$), 489 (M−17), 449 (M−57). |
| 30 | 0.03(12H, s), 0.84(18H), 1.0-3.0(19H, m), 3.4-4.5(3H, m), 4.7-5.1(2H, m), 5.2-5.35(2H, m). | 3440, 3080, 1255, 1110, 835, 770. | 520(M$^+$), 503, (M−17), 463 (M−57). |
| 31 | 0.03(12H, s), 0.84(21H), 1.0-3.0(16H, m), 1.11(3H, s), 3.4-4.5(2H, m), 4.7-5.1(2H, m), 5.2-5.35(2H, m). | 3430, 3080, 1255, 1110, 835, 770. | 522(M$^+$), 505 (M−17), 465 (M−57). |
| 32 | 0.03(12H, s), 0.84(21H), 1.0-3.0(16H, m), 3.4-4.5(2H, m), 4.6-5.5(7H, m). | 3420, 3080, 1255, 1110, 835, 770. | 534(M$^+$), 517 (M−17), 477 (M−57). |
| 33 | 0.03(12H, s), 0.84(21H), 1.0-3.0(16H, m), 1.20(3H, s), 3.4-4.5(2H, m), 4.7-5.1(2H, m), 5.2-5.35(2H, m). | 3420, 3080, 1255, 1110, 835, 770. | 522(M$^+$), 505 (M−17), 465 (M−57). |
| 34 | 0.03(12H, s), 0.84(21H), 1.0-3.0(15H, m), | 3420, 3080, 1255, 1110, | 536(M$^+$), 519 |

TABLE 3-continued 2-hydroxy-3-methylenebicyclo[3.3.0]octanes

| Example | $^1$H NMR (CDCl$_3$, δ (ppm)) | IR (liquid film, cm$^{-1}$) | MS |
|---|---|---|---|
| | 1.13(6H, s), 3.4–4.5(3H, m), 4.7–5.1(2H, m), 5.2–5.35(2H, m). | 835, 770. | (M−17), 479 (M−57). |

TABLE 4

2-oxo-3-methylenebicyclo[3.3.0]octanes

| Example | $^1$H NMR (CDCl$_3$, δ (ppm)) | IR (liquid film, cm$^{-1}$) | MS |
|---|---|---|---|
| 35 | 0.04(12H, s), 0.86(24H), 1.0–2.8(16H, m), 3.5–4.2(2H, m), 5.16(1H, m), 5.2–5.5(2H, m), 5.83(1H, m). | 1725, 1640, 1255, 1115, 1070, 835, 770. | 534(M+), 477 (M−57). |
| 36 | 0.04(12H, s), 0.86(24H), 1.0–2.8(16H, m), 3.5–4.2(2H, m), 5.16(1H, m), 5.2–5.5(2H, m), 5.83(1H, m). | 1725, 1640, 1255, 1115, 1070, 835, 770. | 534(M+), 477 (M−57). |
| 37 | 0.04(12H, s), 0.85(18H), 1.0–2.8(16H, m), 3.5–4.5(2H, m), 5.16(1H, m), 5.2–5.5(2H, m), 5.83(1H, m). | 1725, 1640, 1255, 1115, 1070, 835, 770. | 504(M+), 447 (M−57). |
| 38 | 0.04(12H, s), 0.85(18H), 1.0–2.8(18H, m), 3.5–4.2(2H, m), 5.16(1H, m), 5.2–5.5(2H, m), 5.83(1H, m). | 1725, 1640, 1255, 1115, 1070, 835, 770. | 518(M+), 461 (M−17). |
| 39 | 0.04(12H, s), 0.84(21H), 1.0–2.8(15H, m), 1.11(3H, s), 3.6–4.1(1H, m), 5.16(1H, m), 5.2–5.5(2H, m). | 1725, 1640, 1255, 1115, 1070, 835, 770. | 520(M+), 463 (M−57). |
| 40 | 0.03(12H, s), 0.84(21H), 1.0–2.8(15H, m), 3.6–4.1(1H, m), 4.6–5.5(6H, m), 5.83(1H, m). | 1725, 1640, 1255, 1115, 1070, 835, 770. | 532(M+), 475 (M−57). |
| 41 | 0.03(12H, s), 0.84(21H), 1.0–2.8(15H, m), 1.20(3H, s), 3.6–4.1(1H, m), 5.16(1H, m), 5.2–5.5(2H, m), 5.83(1H, m). | 1725, 1640, 1255, 1115, 1070, 835, 770. | 520(M+), 463 (M−57). |
| 42 | 0.03(12H, s), 0.84(21H), 1.0–2.8(14H, m), 1.13(6H, s), 3.5–4.2(2H, m), 5.16(1H, m), 5.2–5.5(2H, m), 5.83(1H, m). | 1725, 1640, 1255, 1115, 1070, 835, 770. | 534(M+) 477 (M−57). |

TABLE 5

2-acetoxy-3-methylenebicyclo[3.3.0]octanes

| Example | $^1$H NMR (CDCl$_3$, δ (ppm)) | IR (liquid film, cm$^{-1}$) | MS |
|---|---|---|---|
| 43 | 0.05(12H, s), 0.85(24H), 1.0–2.8(16H, m), 1.96(3H, s), 3.4–4.1(3H, m), 4.8–5.1(2H, m), 5.2–5.4(2H, m). | 3080, 1740, 1255, 1235, 1120, 835, 770. | 578(M+), 521 (M−57), 518. |
| 44 | 0.05(12H, s), 0.85(24H), 1.0–2.8(16H, m), 1.96(3H, s), 3.4–4.1(3H, m), 4.8–5.1(2H, m), 5.2–5.4(2H, m). | 3080, 1740, 1255, 1235, 1120, 835, 770. | 578(M+), 521 (M−57), 518. |
| 45 | 0.04(12H, s), 0.84(18H), 1.0–2.8(16H, m), 1.97(3H, s), 3.4–4.1(3H, m), 4.8–5.1(2H, m), 5.2–5.4(2H, m). | 3080, 1740, 1255, 1235, 1120, 835, 770. | 548(M+), 491 (M−57), 488. |
| 46 | 0.03(12H, s), 0.84(18H), 1.0–2.8(18H, m), 1.98(3H, s), 3.4–4.1(3H, m), 4.8–5.1(2H, m), 5.2–5.4(2H, m). | 3080, 1740, 1255, 1235, 1120, 835, 770. | 562(M+), 505 (M−57), 502. |
| 47 | 0.03(12H, s), 0.84(21H), 1.0–2.8(15H, m), 1.11(3H, s), 1.98(3H, s), 3.4–4.1(2H, m), 4.8–5.1(2H, m), 5.2–5.4(2H, m). | 3080, 1740, 1255, 1235, 1120, 835, 770. | 564(M+), 507 (M−57), 504. |
| 48 | 0.03(12H, s), 0.84(21H), 1.0–2.8(15H, m), 1.96(3H, s), 3.4–4.1(2H, m), 4.6–5.5(7H, m). | 30 0, 1740, 1255, 1235, 1120, 835, 770. | 576(M+), 519 (M−57), 516. |
| 49 | 0.03(12H, s), 0.84(21H), 1.0–2.8(15H, m), 1.20(3H, s), 1.97(3H, s), 3.4–4.1(2H, m), 4.8–5.1(2H, m), 5.2–5.4(2H, m). | 3080, 1740, 1255, 1235, 1120, 835, 770. | 564(M+), 507 (M−57), 504. |
| 50 | 0.03(12H, s), 0.84(21H), 1.0–2.9(14H, m), 1.13(6H, s), 1.97(3H, s), 3.4–4.1(3H, m), 4.8–5.1(2H, m), 5.2–5.4(2H, m). | 3080, 1740, 1255, 1235, 1120, 835, 770. | 578(M+), 521 (M−57), 518. |

TABLE 6

2-methanesulfonyloxy-3-methylenebicyclo[3.3.0]-octanes

| Example | $^1$H NMR (CDCl$_3$, δ (ppm)) | IR (liquid film, cm$^{-1}$) | MS |
|---|---|---|---|
| 51 | 0.04(12H, s), 0.85(24H), 1.0–3.0(16H, m), 2.93(3H, s), 3.4–4.5(3H, m), 4.7–5.1(2H, m), 5.2–5.35(2H, m). | 3080, 1355, 1255, 1175, 1115, 960, 830, 770. | 614(M+), 557 (M−57). |
| 52 | 0.04(12H, s), 0.85(24H), 1.0–3.0(16H, m), 2.93(3H, s), 3.4–4.5(3H, m), 4.7–5.1(2H, m), 5.2–5.35(2H, m). | 3080, 1355, 1255, 1175, 1115, 960, 830, 770. | 614(M+), 557 (M−57). |
| 53 | 0.03(12H, s), 0.84(18H), 1.0–3.0(16H, m), 2.93(3H, s), 3.4–4.5(3H, m), 4.7–5.1(2H, m), 5.2–5.35(2H, m). | 3080, 1355, 1255, 1175, 1115, 960, 830, 770. | 584(M+), 527 (M−57). |
| 54 | 0.03(12H, s), 0.84(21H), 1.0–3.0(15H, m), 1.12(3H, s), 2.93(3H, s), 3.4–4.5(2H, m), 4.7–5.1(2H, m), 5.2–5.35(2H, m). | 3080, 1355, 1255, 1175, 1115, 960, 830, 770. | 600(M+), 543 (M−57). |

TABLE 7

2-p-toluenesulfonyloxy-3-methylenebicyclo-[3.3.0]octanes

| Example | $^1$H NMR (CDCl$_3$, δ (ppm)) | IR (liquid film, cm$^{-1}$) | MS |
|---|---|---|---|
| 55 | 0.03(12H, s), 0.85(24H), 1.0–3.0(16H, m), 2.33(3H, s), 3.4–4.5(3H, m), 4.7–5.1(2H, m), 5.2–5.35(2H, m), 7.13(2H, d, J=9Hz), 7.60(2H, d, J=9Hz). | 3080, 1600, 1355, 1255, 1175, 1115, 965, 835, 770. | 690(M$^+$), 633 (M−57). |
| 56 | 0.03(12H, s), 0.85(24H), 1.0–3.0(16H, m), 2.33(3H, s), 3.4–4.5(3H, m), 4.7–5.1(2H, m), 5.2–5.35(2H, m), 7.13(2H, d, J=9Hz), 7.60(2H, d, J=9Hz). | 3080, 1600, 1355, 1255, 1175, 1115, 965, 835. | 690(M$^+$), 633 (M−57). |
| 57 | 0.03(12H, s), 0.85(18H), 1.0–3.0(16H, m), 2.33(3H, s), 3.4–4.5(3H, m), 4.7–5.1(2H, m), 5.2–5.35(2H, m), 7.13(2H, d, J=9Hz), 7.60(2H, d, J=9Hz). | 3080, 1600, 1355, 1255, 1175, 1115, 965, 835, 770. | 600(M$^+$), 603 (M−57). |
| 58 | 0.03(12H, s), 0.84(21H), 1.0–3.0(15H, m), 1.12(3H, s), 2.33(3H, s), 4.7–5.1(2H, m), 5.2–5.35(2H, m), 7.13(2H, d, J=9Hz), 7.60(2H, d, J=9Hz). | 3080, 1600, 1355, 1255, 1175, 1115, 965, 835. | 676(M$^+$), 619 (M−57). |

TABLE 8

2-diphenylphosphoryloxy-3-methylenebicyclo-[3.3.0]octanes

| Example | $^1$H NMR (CDCl$_3$, δ (ppm)) | IR (liquid film, cm$^{-1}$) | MS |
|---|---|---|---|
| 59 | 0.04(12H, s), 0.84(24H), 1.0–3.0(16H, m), 3.4–4.5(3H, m), 4.7–5.1(2H, m), 5.2–5.35(2H, m), 7.30(10H, s). | 3080, 1660, 1590, 1255, 1190, 1115, 965, 835, 770. | 711 (M−57). |
| 60 | 0.04(12H, s), 0.84(24H), 1.0–3.0(16H, m), 3.4–4.5(3H, m), 4.7–5.1(2H, m), 5.2–5.35(2H, m), 7.30(10H, s). | 3080, 1660, 1590, 1255, 1190, 1115, 965, 835, 770. | 711 (M−57). |
| 61 | 0.04(12H, s), 0.84(18H), 1.0–3.0(16H, m), 3.4–4.5(3H, m), 4.7–5.1(2H, m), 5.2–5.35(2H, m), 7.30(10H, s). | 3080, 1660, 1590, 1255, 1190, 1115, 965, 835, 770. | 681 (M−57). |
| 62 | 0.04(12H, s), 0.84(21H), 1.0–3.0(14H, m), 1.1 (3H, s), 3.4–4.5(2H, m), 4.7–5.1(2H, m), 5.2–5.35(2H, m), 7.13(2H, d, J=9Hz), 7.60(2H, d, J=9Hz). | 3080, 1660, 1590, 1255, 1190, 1115, 965, 835, 770. | 697 (M−57). |

EXAMPLE 63

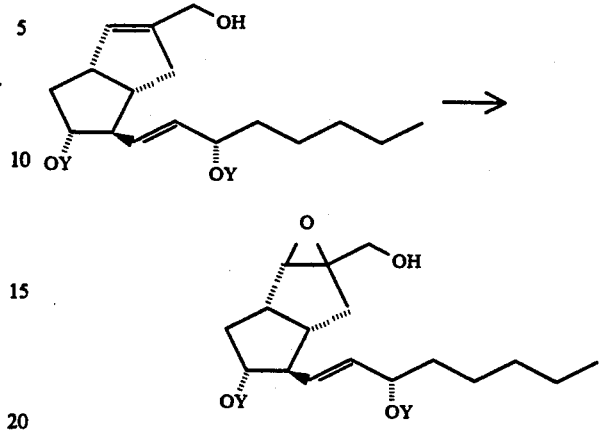

Vanadyl acetylacetonate (10 mg) was added to a solution of (1S,5S,6S,7R)-3-hydroxymethyl-6-[(E,3S)-3-(2-tetrahydropyranyloxy)-1-octenyl]-7-(2-tetrahydropyranyloxy)bicyclo[3.3.01–2-octene (928 mg, 2.00 mmoles) in 8 ml of benzene, and 1 ml (3.0 mmoles) of a 1,2-dichloroethane solution (3.0M) of anhydrous t-butyl hydroperoxide was added at room temperature. The mixture was heated under reflux for 20 minutes. After cooling, the reaction mixture was concentrated, and the resulting crude product was subjected to silica gel column chromatography (silica gel 50 g; hexane/ethyl acetate=6/1) to give (1S,2RS,3RS,5S,6S,7R)-3-hydroxymethyl-2,3-epoxy-6-[(E,3S)-3-(2-tetrahydropyranyloxy)-1-octenyl]-7-(2-tetrahydropyranyloxy)bicyclo[3.3.0]octane (864 mg, 1.80 mmoles, 90%).

NMR(CDCl$_1$ )δ: 0.85(3H,t), 1.0–1.7(20H,m), 1.6–2.7(8H,m), 3.31(1H,m), 3.67(3H,s), 3.4–4.1(6H,m), 4.63(2H,m), 5.15–5.35(2H,m).

IR(liquid film): 3440, 3000, 1135, 1115, 1060, 1000, 965, 860 cm$^{-1}$.

FD-MS: 481(M+1).

EXAMPLE 64

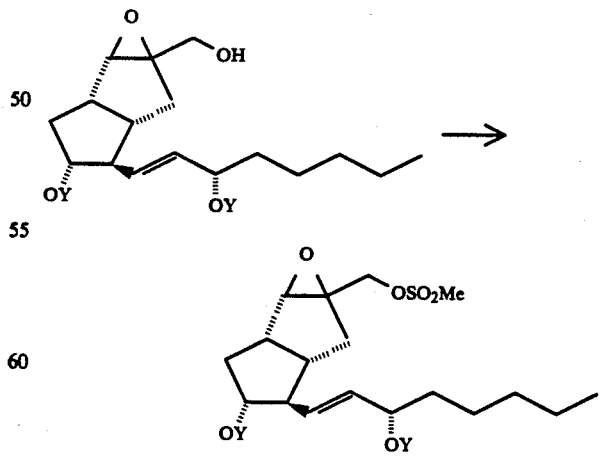

The (1S,2RS,3RS,5S,6S,7R)-3-hydroxymethyl-2,3-epoxy-6-[(E,3S)-3-(2-tetrahydropyranyloxy)1-octenyl]-7-(2-tetrahydropyranyloxy)bicyclo[3.3.0]octane (720 mg, 1.50 mmoles) was dissolved in 3 ml of methylene chloride. The solution was cooled to −250° C., and triethylamine (170 mg, 1.68 mmoles) and then a methylene chloride (3 ml) solution of methanesulfonyl chloride (193 mg, 1.68 mmoles) were added. The mixture was stirred for 1 hour. Ice water was added to the reaction solution, and ethyl acetate was added to perform extraction. The separated organic layer was washed with an aqueous solution of sodium chloride, dried over anhydrous magnesium sulfate, and concentrated to give (1S,2RS,3RS,5S,6S,7R)-3-methane-sulfonyloxymethyl-2,3-epoxy-6-[(E,3S)-3-(2-tetrahydropyranyloxy)bicyclo[3.3.0]octane (820 mg, 1.47 mmoles, 98%).

NMR(CDCl$_1$ )δ: 0.84(3H,t), 1.0–1.7(20H,m), 1.7–2.7(7H,m), 2.94(3H,s), 3.30(1H,m), 3.6–4.1(6H,m), 4.0–4.6(2H,m), 4.60(2H,m), 5.15–5.35(2H,m).

IR(liquid film): 3000, 1735, 1355, 1175, 1135, 1115, 1060, 1000, 960 cm$^{-1}$.

FD-MS: 558(M+).

EXAMPLE 65

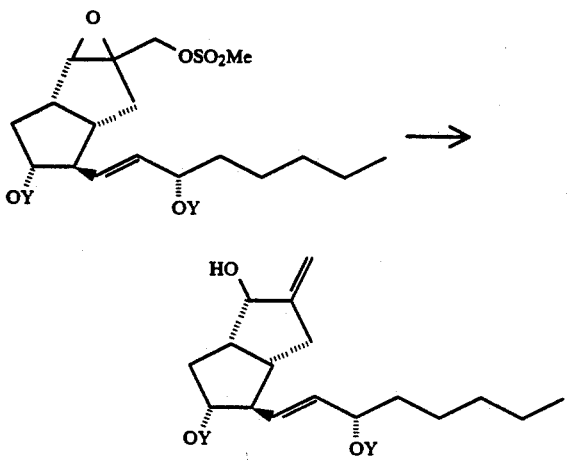

A solution of the (1S,2RS,3RS,5S,6S,7R)-3-methanesulfonyloxymethyl-2,3-epoxy-6-[(E,3S)-3-(2-tetrahydropyranyloxy)-1-octenyl]-7-(2-tetrahydropyranyloxy) bicyclo[3.3.0]octane (781 mg, 1.40 mmoles) in 3 ml of tetrahydrofuran was added to an anion radical solution prepared by reacting naphthalene (1.28 g, 10 mmoles) and sodium (207 mg, 9 mmoles) in 30 ml of tetrahydrofuran at room temperature for 1 hour. The mixture was stirred at room temperature for 10 minutes. To the reaction solution was addded 3.0 g of ammonium chloride, and thereafter, a saturated aqueous solution of ammonium chloride was added. The mixture was worked up and extracted with ethyl acetate. The organic layer was washed with sodium chloride, dried over anhydrous magnesium sulfate, and concentrated to obtain a crude product. The crude product was subjected to column chromatography (silica gel 50 g; hexane/ethyl acetate=19/1) to give (1S,2RS,5S,6S,7R)-2-hydroxy-3-methylene-6-[(E,3S)-3-(2-tetrahydropyranyloxy)-1-octenyl]-7-(2-tetrahydropyranyloxy)bicyclo[3.3.0]octane (520 mg, 1.12 mmoles, 80%).

NMR(CDCl$_3$)δ: 0.85(3H,t), 1.0–3.0(28H,m), 3.4–4.5(7H,m), 4.63(2H,m), 4.7–5.1(2H,m), 5.2–5.35(2H,m).

IR(liquid film): 3350, 3080, 1660, 1135, 1115, 1000, 965, 935 cm$^{-1}$.

FD-MS: 465(M+1).

EXAMPLE 66

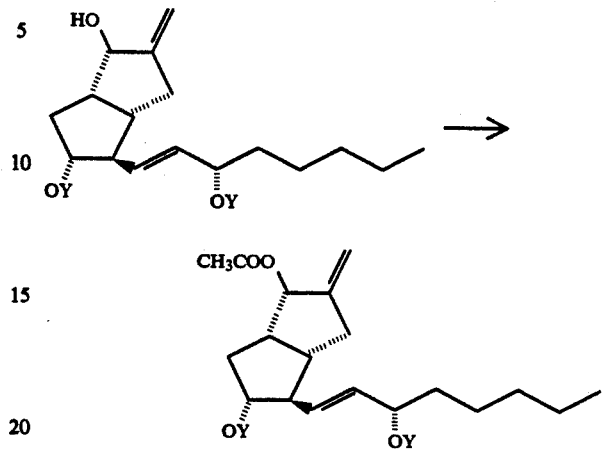

Acetic anhydride (5.0 ml) and pyrdine (5.0 g) were added to the (1S,2RS,5S,6S,7R)-2-hydroxy-3-methylene-6-[(E,3S)-3-(2-tetrahydropyranyloxy)-1-octenyl]-7-(2-tetrahydropyranyloxy)bicyclo[3.3.0]octane (928 mg, 2.00 mmoles) obtained in Example 65, and the mixture was stirred at room temperature for 10 hours. The reaction mixture was concentrated under reduced pressure, and subjected to column chromatography (silica gel 200 g; hexane/ethyl acetate=19/1) to give (1S,2RS,5S,6S,7R)-2-acetoxy-3-methylene-6-[(E,3S)-3-(2-tetrahydropyranyloxy)-1-octenyl]-7-(2-tetrahydropyranyloxy)bicyclo[3.3.0]octane (982 mg, 1.94 mmoles, 97%).

NMR(CDCl$_1$ )δ: 0.84(3H,t), 1.0–2.8(27H,m), 1.95(3H,s), 3.4–4.1(74H,m), 4.60(2H,m), 4.8–5.1(2H,m), 5.2–5.4(2H,m).

IR(liquid film): 3080, 1740, 1660, 1235, 1120, 965, 855, cm$^{-1}$.

FD-MS: 506(M+).

EXAMPLES 67–70

The following compounds 67 and 68 were synthesized by the same way as in Example 7 and the compounds 69 and 70 were synthesized by the same way as in Example 66.

EXAMPLE 67

(1S,2RS,5S,6S,7R)-2-pivaloyloxy-3-methylene-6-[(E,3S)-3-t-butyldimethylsilyloxy-1-octenyl]-7-t-butyldimethylsilyloxybicyclo[3.3.0]octane (96%).

EXAMPLE 68

(1S,2RS,5S,6S,7R)-2-(2,4,6-trimethylbenzoyloxy)-3-methylene-6-[(E,3S)-3-t-butyldimethylsilyloxy-1-octenyl]-7-t-butyldimethylsilyloxybicyclo[3.3.0]octane (91%).

EXAMPLE 69

(1S,2RS,5S,6S,7R)-2-pivaloyloxy-3-methylene-6-[(E,3S)-3-(2-tetrahydropyranyloxy)-1-octenyl]-7-(2-tetrahydropyranyloxy)bicyclo[3.3.0]octane (96%).

EXAMPLE 70

(1S,2RS,5S,6S,7R)-2-(2,4,6-trimethylbenzoyloxy)-3-methylene-6-[(E,3S)-3-(2-tetrahydropyranyloxy)-1- octenyl]-7-(2-tetrahydropyranyloxy)bicyclo[3.3.0]octane (88%).

TABLE 9

2-acyloxy-3-methylenebicyclo[3.3.0]octanes

| Example | $^1$H NMR (CDCl$_3$, δ (ppm)) | IR (liquid film, cm$^{-1}$) | MS |
|---|---|---|---|
| 67 | 0.05(12H, s), 0.84(21H), 1.20(9H, s), 1.0–2.8(15H, m), 3.4–4.1(3H, m), 4.8–5.1(2H, m), 5.2–5.4(2H, m), | 3080, 1740, 1660, 1250, 1235, 1120, 965, 855, 835, 775. | 592(M$^+$), 535, 532. |
| 68 | 0.05(12H, s), 0.84 21H), 2.25(3H, s), 2.33(6H, s), 1.0–2.8(15H, m), 3.4–4.1(3H, m), 4.8–5.1(2H, m), 5.2–5.4(2H, m), 6.80(2H, m). | 3080, 1720, 1660, 1600, 1250, 1235, 1120, 965, 855, 835, 775. | 654(M$^+$), 597, 594. |
| 69 | 0.84(21H), 1.20(9H, s), 1.0–2.8(27H, m), 3.4–4.1(74H, m), 4.60(2H, m), 4.8–5.1(2H, m), 5.2–5.4(2H, m), | 3080, 1740, 1660, 1235, 1120, 965, 855. | 548(M$^+$), |
| 70 | 0.84(3H,t), 2.25(3H, s), 2.33(6H, s), 1.0–2.8(27H, m), 3.4–4.1(74H, m), 4.60(2H, m), 4.8–5.1(2H, m), 5.2–5.4(2H, m), 6.80(2H, m). | 3080, 1720, 1660, 1600, 1235, 1120, 965, 855. | 610(M$^+$), |

EXAMPLES 71–77

Example 3 as repeated except that each of the groups indicated in Table 10 was substituted for the dimethyl-t-butylsilyl group. Compounds of formula (I) in which R$^2$ and R$^3$ are as indicated in Table 10 were obtained.

TABLE 10

| Example | Group used instead of the dimethyl-t-butylsilyl group | R$^2$ and R$^3$ |
|---|---|---|
| 71 | tribenzylsilyl group | same as left |
| 72 | triethylsilyl group | " |
| 73 | t-butyldiphenylsilyl group | " |
| 74 | dimethylphenylsilyl group | " |
| 75 | methoxymethyl group | " |
| 76 | 1-ethoxyethyl group | " |
| 77 | 2-methoxy-2-propyl group | " |

REFERENTIAL EXAMPLE 1

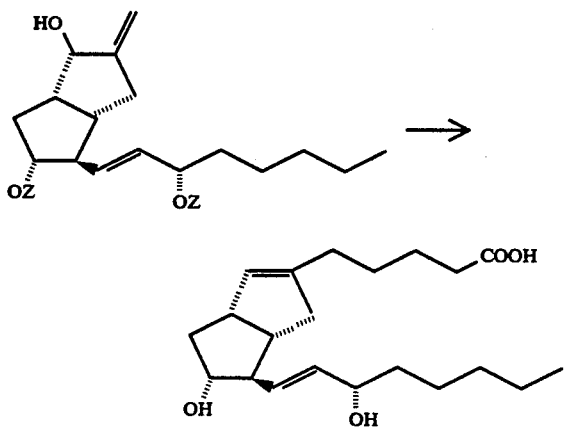

A hexane solution of n-butyllithium (1.56M, 2.72 ml, 4.24 mmoles) was added at 0° C. to a solution of (1S,2RS,5S,6S,7R)-2-hydroxy-3-methylene-6-[(E,3S)-3-t-butyldimethylsilyloxy-1-octenyl]-7-t-butyldimethylsilyloxybicyclo[3.3.0]octane (1.80 g, 3.54 mmoles) in 50 ml of tetrahydrofuran, and the mixture was stirred at room temperature for 30 minutes. The solution was added to a suspension of cuprous iodide (1.01 g, 5.31 mmoles) cooled at −78° C. The temperature of the mixture was elevated to room temperature, and it was stirred for 30 minutes.

Separately, prior to the above procedure, metallic lithium (350 mg, 50.0 mmoles) was added to room temperature to a solution of naphthalene (6.41 g, 50.0 mmoles) in 50 ml of tetrahydrofuran at room temperature. After the mixture was colored, it was cooled to 0° C. and stirred for 5 hours. A solution of 4-bromo-1-butene (3.38 g, 25.0 mmoles) in 50 ml of tetrahydrofuran was added dropwise at −78° C. to the resulting solution, and the mixture was stirred at −78° C. for 5 minutes. The resulting solution was added dropwise at −78° C. to the solution prepared by the procedure of the first paragraph, and the mixture was stirred for 10 minutes. A solution of N-methyl-N-phenylamino-tributylphosphonium iodide (4.61 g, 10.6 mmoles) in 30 ml of N,N-dimethylformamide was added to the mixture. The cooling bath was removed, and the temperature was elevated. The mixture was then stirred at room temperature for 3 hours.

A saturated aqueous solution of ammonium chloride was added to the reaction solution, and the mixture was extracted with hexane. The resulting organic layer was washed with an aqueous solution of sodium chloride, dried over anhydrous magnesium sulfate and concentrated to give a crude product. The crude product was subjected to column chromatography (silica gel treated with triethylamine; hexane/ether=9/1) to give (1S,5S,6S,7R)-3-(4-pentenyl)-6-[(E,3S)-3-t-butyldimethylsilyloxy-1-octenyl]-7-t-butyldimethylsilyloxybicyclo[3.3.01-2-octene (1.16 g, 2.12 mmoles, 60%).

NMR(CDCl$_3$)δ:
0.03(12H,s), 0.83(21H,m), 1.0–3.1(21H,m), 3.1–4.2(2H,m), 4.6–6.0(6H,m).

Thus obtained compound was converted into a corresponding 9(0)-methano-Δ$^{6(9α)}$-prostaglandin I$_1$ according to the same procedure as disclosed in Tetrahedron Letters, 25, 5087(1984) by M. Shibasaki et al. This product was completely identical with an authentic sample.

NMR(CDCl$_3$)δ: 0.83(3H,m), 1.0–3.3(23H,m), 3.3–4.3(2H,m), 5.20(1H,bs), 5.25–5.5(2H,m), 5.97(3H,bs).

IR(liquid film): 3350, 3050, 1710, 1090, 970 cm$^{-1}$.

REFERENTIAL EXAMPLES 2–9

According to the procedure of Referential Example 1, various kinds of 9(0)-methano-Δ$^{6(9α)}$-prostaglandin I$_1$ derivatives listed in the Table 11 below were obtained by using corresponding starting materials listed in the same table.

TABLE 11

| No. | 9(O)-methano-$\Delta^{6(9\alpha)}$-PGI$_1$ derivative | starting material |
|---|---|---|
| 2 | 17(R),20-dimethyl-9(O)-methano-$\Delta^{6(9\alpha)}$-prostaglandin I$_1$ | (1S,2RS,3RS,5S,6S,7R)-2-hydroxy-3-methylene-6-[(E,3S,5R)-3-t-butyldimethylsilyloxy-5-methyl-1-nonenyl]-7-t-butyldimethylsilyloxybicyclo[3.3.0]octane |
| 3 | 17(S),20-dimethyl-9(O)-methano-$\Delta^{6(9\alpha)}$-prostaglandin I$_1$ | (1S,2RS,3RS,5S,6S,7R)-2-hydroxy-3-methylene-6-[(E,3S,5S)-3-t-butyldimethylsilyloxy-5-methyl-1-nonenyl]-7-t-butyldimethylsilyloxybicyclo[3.3.0]octane |
| 4 | 16,17,18,19,20-pentanor-15-cyclopentyl-9(O)-methano-$\Delta^{6(9\alpha)}$-prostaglandin I$_1$ | (1S,2RS,3RS,5S,6S,7R)-2-hydroxy-3-methylene-6-[(E,3S)-3-t-butyldimethylsilyloxy-3-cyclopentyl-1-propenyl]-7-t-butyldimethylsilyloxybicyclo-[3.3.0]octane |
| 5 | 16,17,18,19,20-pentanor-15-cyclohexyl-9(O)-methano-$\Delta^{6(9\alpha)}$-prostaglandin I$_1$ | (1S,2RS,3RS,5S,6S,7R)-2-hydroxy-3-methylene-6-[(E,3S)-3-t-butyldimethylsilyloxy-3-cyclohexyl-1-propenyl]-7-t-butyldimethylsilyloxybicyclo-[3.3.0]octane |
| 6 | 15-deoxy-16-hydroxy-16-methyl-9(O)-methano-$\Delta^{6(9\alpha)}$-prostaglandin I$_1$ | (1S,2RS,3RS,5S,6S,7S)-2-hydroxy-3-methylene-6-[(E)-4-butyldimethylsilyloxy-4-methyl-1-octenyl]-7-t-butyldimethylsilyloxybicyclo[3.3.0]octane |
| 7 | 15-deoxy-16-hydroxy-16-vinyl-9(O)-methano-$\Delta^{6(9\alpha)}$-prostaglandin I$_1$ | (1S,2RS,3RS,5S,6S,7R)-2-hydroxy-3-methylene-6-[(E)-4-t-butyldimethylsilyloxy-4-vinyl-1-octenyl]-7-t-butyldimethylsilyloxybicyclo[3.3.0]octane |
| 8 | 15-methyl-9(O)-methano-$\Delta^{6(9\alpha)}$-prostaglandin I$_1$ | (1S,2RS,3RS,5S,6S,7R)-2-hydroxy-3-methylene-6-[(E)-3-t-butyldimethylsilyloxy-3-methyl-1-octenyl]-7-t-butyldimethylsilyloxybicyclo[3.3.0]octane |
| 9 | 16,16-dimethyl-9(O)-methano-$\alpha 66^{6(9\alpha)}$-prostaglandin I$_1$ | (1S,2RS,3RS,5S,6S,7R)-2-hydroxy-3-methylene-6-[(E)-3-t-butyldimethylsilyloxy-4,4-dimethyl-1-octenyl]-7-t-butyldimethylsilyloxybicyclo[3.3.0]octane |

What we claim is:

1. A 2,6,7-trisubstituted-3-methylenebicyclo(3.3.0)octane which is a compound represented by the following formula (I)

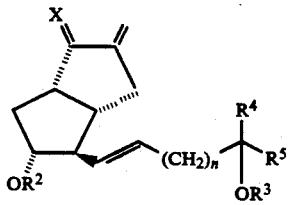

wherein R$^2$ and R$^3$ are identical or different and each represents a hydrogen atom, a tri(C$_1$-C$_7$)-hydrocarbonsilyl group or a group forming an acetal linkage together with the oxygen atom to which it is bonded; R$^4$ represents a hydrogen atom, a methyl group or a vinyl group; R$^5$ represents (a) an unsubstituted linear or branched C$_3$-C$_8$ alkyl group which may be interrupted by an oxygen atom, (b) a substituted linear or branched C$_1$-C$_5$ alkyl group in which the substituent is a C$_1$-C$_6$ alkoxy group or a phenyl, phenoxy or C$_3$-C$_{10}$ cycloalkyl group which may be substituted by a halogen atom, a protected hydroxyl group or a C$_1$-C$_4$ alkyl group, (c) a phenyl group which may be substituted by a halogen atom, a protected hydroxyl group or a C$_1$-C$_4$ alkyl group, or (e) a C$_3$-C$_{10}$ cycloalkyl group which may be substituted by a halogen atom, a protected hydroxyl group or a C$_1$-C$_4$ alkyl group; n is 0 or 1; and X= represents an oxo group (O=) or a group of the formula

in which R$^1$ represents a hydrogen atom, a tri-(C$_1$-C$_7$-)hydrocarbonsilyl group, a group forming an acetal linkage together with the oxygen atom to which it is bonded, a C$_2$-C$_{10}$ acyl group, a (C$_1$-C$_{10}$)-hydrocarbonsulfonyl group, or a di(C$_1$-C$_{10}$) hydrocarbonphosphoryl group, or an enantiomer thereof, or a mixture of these.

2. The octane of claim 1 wherein X= is an oxo (O=) group.

3. The octane of claim 1 wherein X= is the group

in which R$^1$ is as defined.

4. The octane of claim 3 wherein R$^1$ is a hydrogen atom or a C$_2$-C$_{10}$ acyl group.

5. The octane of claim 1 wherein R$^2$ and R$^3$ are identical or different, and each represents a hydrogen atom, a tri(C$_1$-C$_4$)alkylsilyl group, a diphenyl(C$_1$-C$_4$)alkylsilyl group, a phenyldi(C$_1$-C$_4$)alkylsilyl group, a 2-tetrahydropyranyl group, a 2-tetrahydrofuranyl group, a 1-ethoxyethyl group, a 2-ethoxy-2-propyl group, a (2-methoxyethoxy)methyl group, or a 6,6-dimethyl-3-oxa-2-oxobicyclo[3.1.0]hex-4-yl group.

6. The octane of claim 1 wherein R$^4$ is a hydrogen atom.

7. The octane of claim 1 wherein R$^4$ is a methyl group.

8. The octane of claim 1 wherein R$^4$ is a vinyl group.

9. The octane of claim 1 wherein R$^5$ represents (b) a linear or branched C$_1$-C$_5$ alkyl group which is substituted by (i) unsubstituted or (ii) substituted phenyl, phenoxy or C$_3$-C$_{10}$ cycloalkyl group, (d) a phenoxy group which may be substituted by a halogen atom, a protected hydroxyl group or a C$_1$-C$_4$ alkyl group, or (e)

a $C_3$–$C_{10}$ cycloalkyl group which may be substituted by a halogen atom, a protected hydroxyl group or a $C_1$–$C_4$ alkyl group, and the substituent of the (ii) substituted phenyl, phenoxy or $C_3$–$C_{10}$ cycloalkyl group is a halogen atom, a tri($C_1$–$C_7$)hydrocarbonsilyloxy group, a $C_1$–$C_4$ alkyl group or a $C_1$–$C_6$ alkoxy group.

10. The octane of claim 1 wherein n is 0.

11. The octane of claim 1 wherein n is 1.

12. The octane of claim 1 which has the optical configuration represented by the above formula (I).

13. The octane of claim 1 which is (1S,2RS,5S,6S,7R)-2-hydroxy-3-methylene-6-[(E,3S)-3-t-butyldimethylsilyloxy-1-octenyl)-7-t-butyldimethylsilyloxybicyclo[3.3.0]octane.

14. The octane of claim 1 which is (1S,5S,6S,7R)-2-oxo-3-methylene-6-[(E,3S)-3-t-butyldimethylsilyloxy-1-octenyl]-7-t-butyldimethylsilyloxybicyclo[3.3.0]octane.

15. The octane of claim 1 which is (1S,2RS,5S,6S,7R)-2-hydroxy-3-methylene-6-[(E,3S)-3-t-butyldimethylsilyloxy-1-octenyl]-7-t-butyldimethylsilyloxybicyclo[3.3.0]octane.

16. The octane of claim 1 which is (1S,2RS,5S,6S,7R)-2-(2-tetrahydropyranyloxy)-3-methylene-6[(E,3S)-3-t-butyldimethylsilyloxy-1-octenyl]-7-t-butyl-7-t-butyldimethylsilyloxybicyclo[3.3.0 octane.

17. The octane of claim 1 wherein $R^2$ and $R^3$ represent t-butyldimethylsilyl.

18. The octane of claim 1 wherein $R^2$ and $R^3$ represent 2-tetrahydropyranyl.

19. The octane of claim 1 wherein $R^2$ and $R^3$ represent a hydrogen atom.

20. The octane of claim 19 wherein X= represents an oxo group.

21. The octane of claim 19 wherein X= represents

* * * * *